US012667343B2

(12) United States Patent
Zhou et al.

(10) Patent No.: US 12,667,343 B2
(45) Date of Patent: Jun. 30, 2026

(54) SUPPRESSING INTERFERENCE ARTIFACTS IN ULTRASOUND

(71) Applicant: FUJIFILM SONOSITE, INC., Bothell, WA (US)

(72) Inventors: Yong Zhou, Woodinville, WA (US); Jean Tsou, Seattle, WA (US); Andrew Lundberg, Woodinville, WA (US); Thomas Endres, Sagle, ID (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 18/473,694

(22) Filed: Sep. 25, 2023

(65) Prior Publication Data

US 2025/0099080 A1 Mar. 27, 2025

(51) Int. Cl.
*A61B 8/00* (2006.01)

(52) U.S. Cl.
CPC ............ *A61B 8/5269* (2013.01); *A61B 8/463* (2013.01); *A61B 8/467* (2013.01); *A61B 8/5207* (2013.01)

(58) Field of Classification Search
CPC .................................................. A61B 8/5269
See application file for complete search history.

(56) References Cited

U.S. PATENT DOCUMENTS

| | | | | | |
|---|---|---|---|---|---|
| 5,445,156 A | * | 8/1995 | Daft | .................... | G01S 7/52071 |
| | | | | | 600/454 |
| 6,039,692 A | * | 3/2000 | Kristoffersen | .......... | G01S 15/52 |
| | | | | | 600/454 |
| 6,142,942 A | * | 11/2000 | Clark | .................. | G01S 7/52025 |
| | | | | | 600/443 |
| 6,267,725 B1 | * | 7/2001 | Dubberstein | ....... | G01S 7/52033 |
| | | | | | 600/443 |
| 6,296,612 B1 | * | 10/2001 | Mo | ..................... | G01S 15/8981 |
| | | | | | 600/455 |
| 2008/0059098 A1 | * | 3/2008 | Zhang | ................. | G01S 7/52077 |
| | | | | | 702/103 |
| 2010/0074240 A1 | * | 3/2010 | Jian | ...................... | H04B 1/0057 |
| | | | | | 370/339 |
| 2011/0231160 A1 | * | 9/2011 | Suzuki | ................. | A61B 5/7203 |
| | | | | | 702/189 |
| 2011/0313292 A1 | * | 12/2011 | Kwak | ................. | G01S 15/8981 |
| | | | | | 600/453 |

(Continued)

*Primary Examiner* — Nyrobi Celestine
(74) *Attorney, Agent, or Firm* — Womble Bond Dickinson (US) LLP

(57) ABSTRACT

An ultrasound system includes an ultrasound scanner configured to transmit ultrasound at a patient anatomy and receive reflections of the ultrasound from the patient anatomy. The ultrasound system includes an ultrasound machine configured to generate received data including ultrasound data based on the reflections of the ultrasound and artifact data based on an interferer. The ultrasound system includes a processor system that is implemented to determine an artifact signal that is based on the interferer, determine, based on the artifact signal, one or more artifact characteristics. In some embodiments, the artifact characteristics are selected from the group consisting of an amplitude, a phase, a center frequency, and a bandwidth. The processor system is implemented to generate, based on the artifact characteristics, filter coefficients, and filter, based on the filter coefficients, the received data to suppress the artifact data and recover the ultrasound data.

17 Claims, 19 Drawing Sheets

(56)         References Cited

U.S. PATENT DOCUMENTS

| | | | |
|---|---|---|---|
| 2015/0289849 A1* | 10/2015 | Taniguchi | G01S 7/52038 |
| | | | 600/443 |
| 2016/0328643 A1* | 11/2016 | Liu | G06T 7/0012 |
| 2017/0135672 A1* | 5/2017 | Pelissier | A61B 8/14 |
| 2018/0253830 A1* | 9/2018 | Courtney | G06T 5/70 |
| 2019/0328368 A1* | 10/2019 | Pedersen | G16H 50/30 |
| 2020/0083862 A1* | 3/2020 | Makkonen | H03H 9/173 |
| 2020/0261061 A1* | 8/2020 | Shin | A61B 8/5269 |
| 2022/0361850 A1* | 11/2022 | Takeda | A61B 8/5223 |

* cited by examiner

610

620

Extra line of pixels
(not displayed)
621

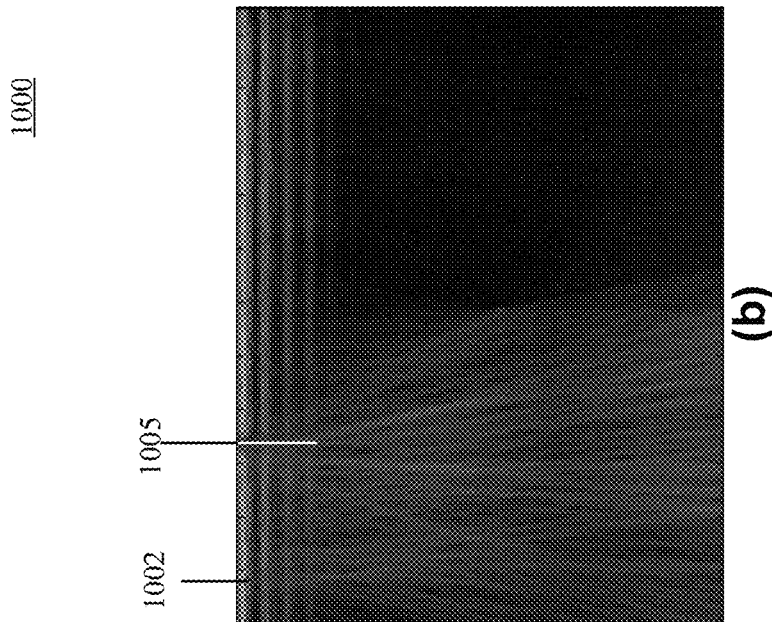
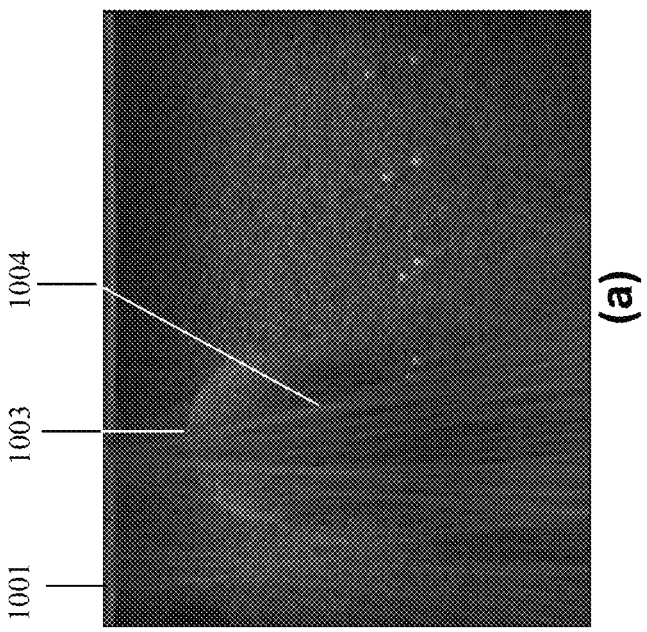
FIG. 10

Figure 13:
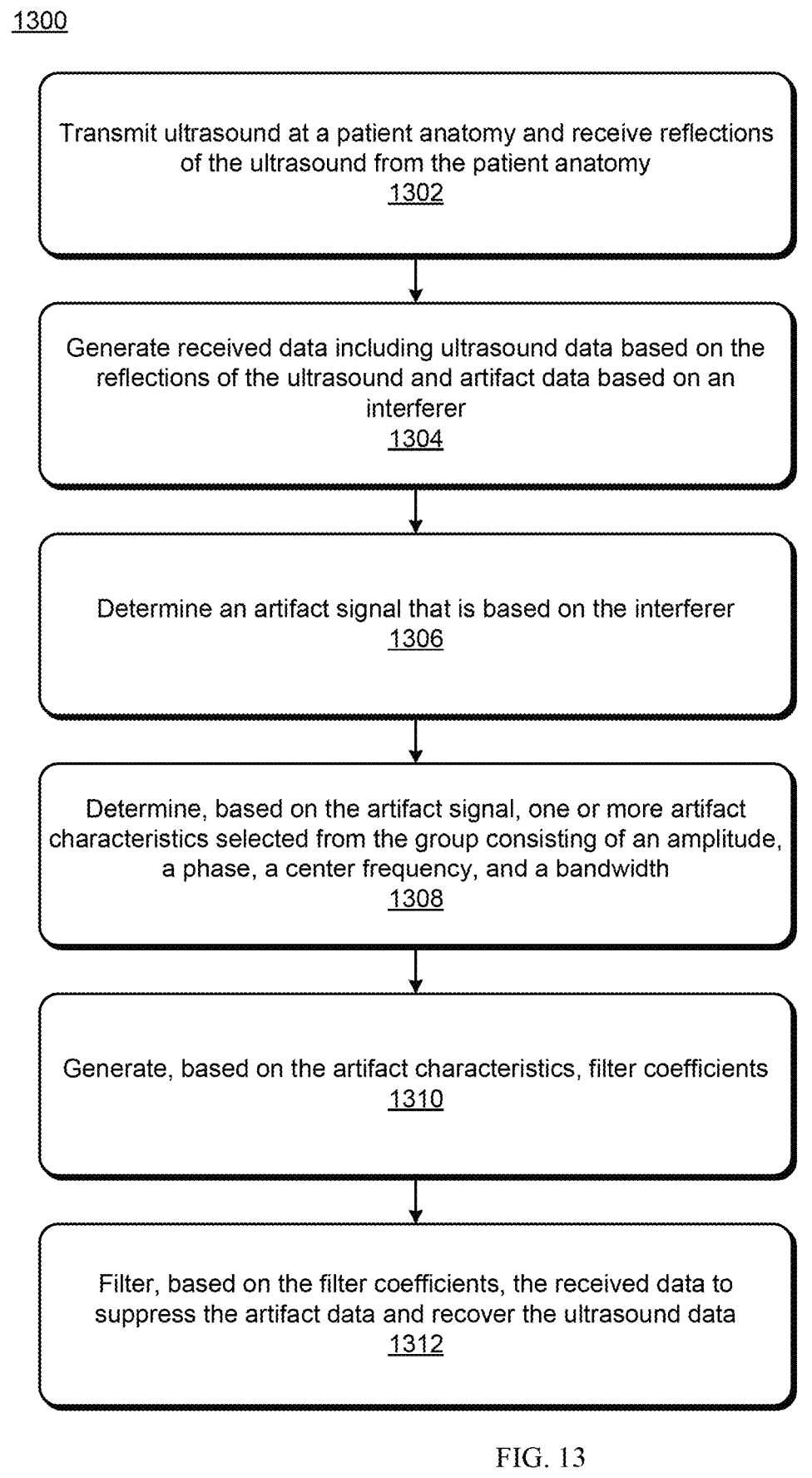

1300

Transmit ultrasound at a patient anatomy and receive reflections
of the ultrasound from the patient anatomy
1302

↓

Generate received data including ultrasound data based on the
reflections of the ultrasound and artifact data based on an
interferer
1304

↓

Determine an artifact signal that is based on the interferer
1306

↓

Determine, based on the artifact signal, one or more artifact
characteristics selected from the group consisting of an amplitude,
a phase, a center frequency, and a bandwidth
1308

↓

Generate, based on the artifact characteristics, filter coefficients
1310

↓

Filter, based on the filter coefficients, the received data to
suppress the artifact data and recover the ultrasound data
1312

Figure 14:
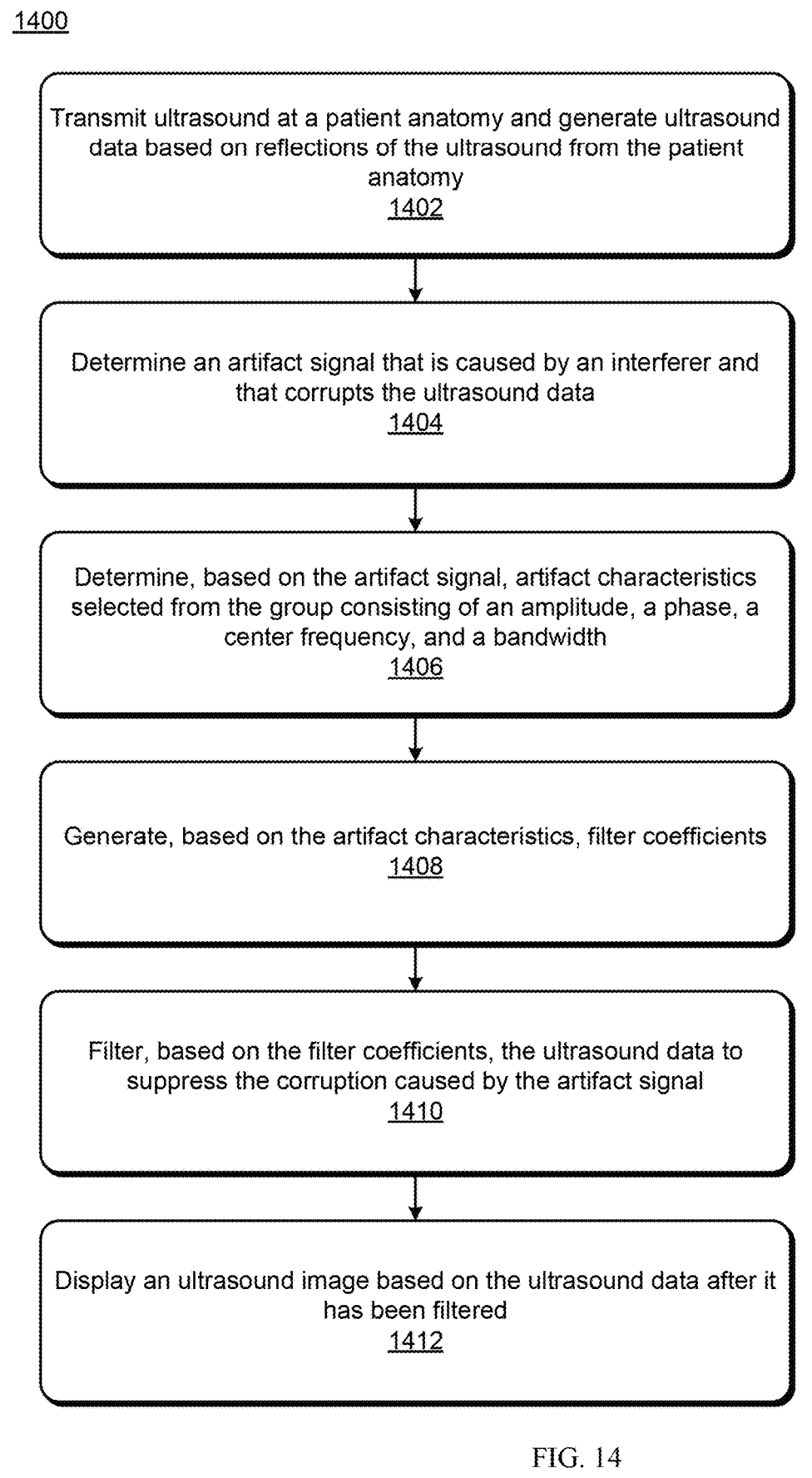

Transmit ultrasound at a patient anatomy and generate ultrasound data based on reflections of the ultrasound from the patient anatomy
1402

Determine an artifact signal that is caused by an interferer and that corrupts the ultrasound data
1404

Determine, based on the artifact signal, artifact characteristics selected from the group consisting of an amplitude, a phase, a center frequency, and a bandwidth
1406

Generate, based on the artifact characteristics, filter coefficients
1408

Filter, based on the filter coefficients, the ultrasound data to suppress the corruption caused by the artifact signal
1410

Display an ultrasound image based on the ultrasound data after it has been filtered
1412

Figure 15:
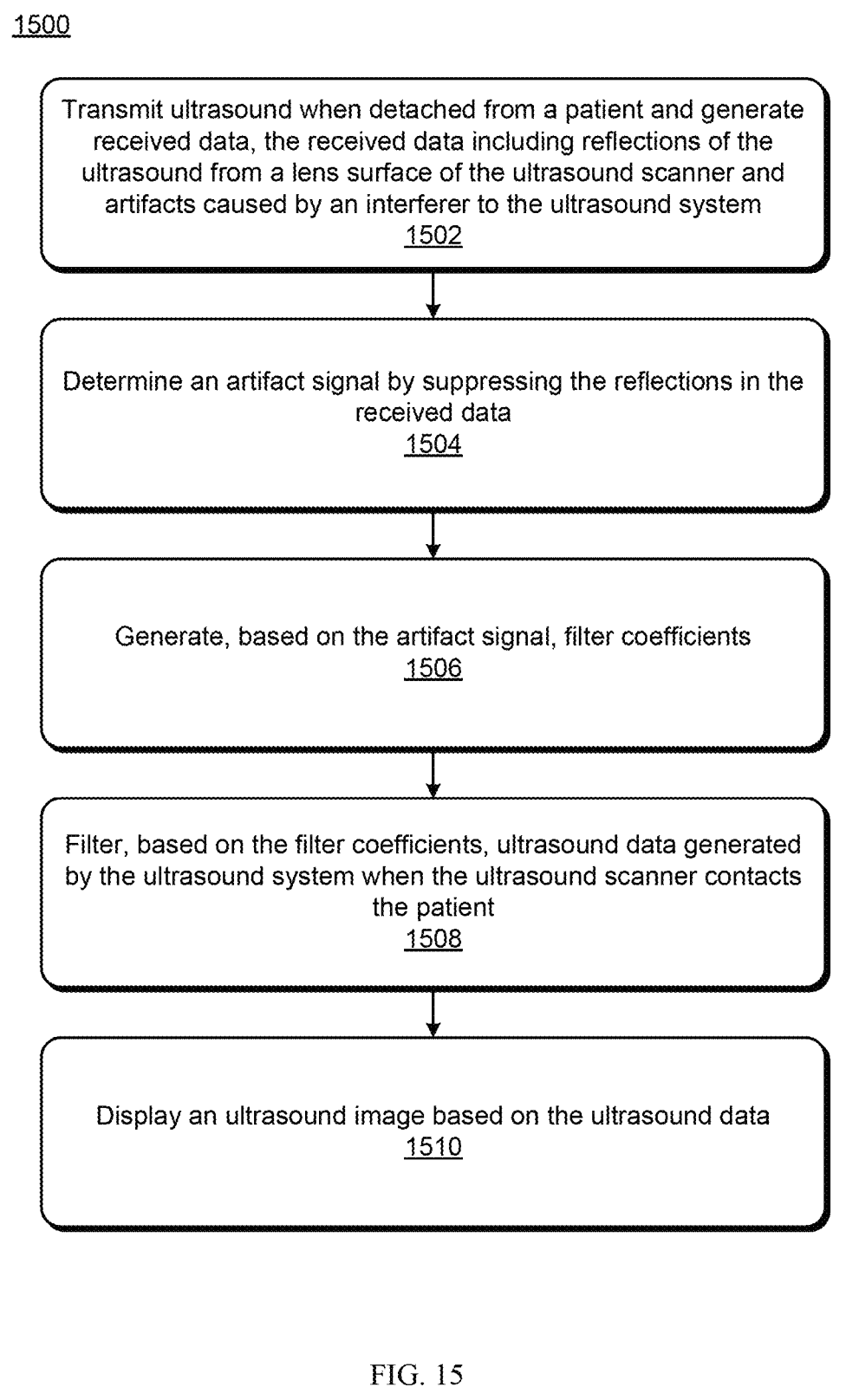

Transmit ultrasound when detached from a patient and generate received data, the received data including reflections of the ultrasound from a lens surface of the ultrasound scanner and artifacts caused by an interferer to the ultrasound system
1502

Determine an artifact signal by suppressing the reflections in the received data
1504

Generate, based on the artifact signal, filter coefficients
1506

Filter, based on the filter coefficients, ultrasound data generated by the ultrasound system when the ultrasound scanner contacts the patient
1508

Display an ultrasound image based on the ultrasound data
1510

Processing device (e.g., one or more processors, neural networks, etc.)
1602

Instructions
1626

Main Memory
1604

Instructions
1626

Static Memory
1606

Network Interface Device
1608

Network
1620

Video Display Device
1610

Alpha-Numeric Input Device
1612

Cursor Control Device
1614

Signal Generation Device
1616

Data Storage Device
1618

Machine-Readable Storage Medium
1628

Instructions
1626

SUPPRESSING INTERFERENCE ARTIFACTS IN ULTRASOUND

Embodiments disclosed herein relate to ultrasound systems. More specifically, embodiments disclosed herein relate to suppressing interference artifacts in ultrasound.

BACKGROUND

Generally, ultrasound imaging is a widely used non-ionizing diagnostic tool. Typically, in ultrasound imaging, the image quality not only can be impacted by system noise, such as electronic noise and speckle noise, but also can be impacted by inside and outside artifacts, such as artifacts from other medical devices, for example, a surgical knife, an intravascular catheter, a patient monitoring system, and non-medical devices, for example, consumer electrical devices and radio-frequency identification (RFID) scanners. These artifacts can be severe and prevent further ultrasound scanning. In addition, there are more scenarios where ultrasound imaging and other medical devices are used together to provide more patient information and enable performing treatment at the same time as a diagnosis. Furthermore, more and more hospitals use RFID to track the equipment. All the above may potentially cause more artifacts in the ultrasound imaging.

Typically, the artifacts frequencies are not constant from different artifacts sources (e.g., interferers). For example, for an RFID reader, the ultrasound artifacts are typically at 13.56 MHz; however, for surgical knife, the artifacts often range within all the system acceptance frequency band. Thus, a traditional single frequency/bandwidth filter will not adequately suppress the artifacts.

Conventional ultrasound systems do not have filters to effectively mitigate the artifacts during ultrasound imaging. Hence, the conventional ultrasound systems may not produce usable ultrasound images, so that patients may not receive the best care possible.

SUMMARY

Systems and methods to suppress interference artifacts in ultrasound systems are described. In some embodiments, an ultrasound system includes an ultrasound scanner configured to transmit ultrasound at a patient anatomy and receive reflections of the ultrasound from the patient anatomy. The ultrasound system also includes an ultrasound machine configured to generate received data including ultrasound data based on the reflections of the ultrasound and artifact data based on an interferer. The ultrasound system also includes a processor system that is implemented to determine an artifact signal that is based on the interferer, and determine, based on the artifact signal, artifact characteristics. In some embodiments, the artifact characteristics are selected from the group consisting of an amplitude, a phase, a center frequency, and a bandwidth. The processor system is implemented to generate, based on the artifact characteristics, filter coefficients, and filter, based on the filter coefficients, the received data to suppress the artifact data and recover the ultrasound data.

In some other embodiments, an ultrasound system includes an ultrasound scanner configured to transmit ultrasound at a patient anatomy and generate ultrasound data based on reflections of the ultrasound from the patient anatomy. The ultrasound system also includes a processor system that is implemented to determine an artifact signal that is caused by an interferer and that corrupts the ultrasound data, and determine, based on the artifact signal, artifact characteristics selected from the group consisting of an amplitude, a phase, a center frequency, and a bandwidth. The processor system is also implemented to generate, based on the artifact characteristics, filter coefficients, and filter, based on the filter coefficients, the ultrasound data to suppress the corruption caused by the artifact signal. The ultrasound system includes a display device implemented to display an ultrasound image based on the ultrasound data after it has been filtered.

In yet some other embodiments, an ultrasound system includes an ultrasound scanner configured to transmit ultrasound when detached from a patient and generate received data. The received data includes reflections of the ultrasound from a lens surface of the ultrasound scanner and artifacts caused by an interferer to the ultrasound system. The ultrasound system further includes a processor system that is implemented to determine an artifact signal by suppressing the reflections in the received data. The processor system is implemented to generate, based on the artifact signal, filter coefficients, and filter, based on the filter coefficients the ultrasound data that is generated by the ultrasound system when the ultrasound scanner contacts the patient. The ultrasound system includes a display device implemented to display an ultrasound image based on the ultrasound data.

Other systems, devices, and methods to suppress interference artifacts in ultrasound systems are also described.

BRIEF DESCRIPTION OF THE DRAWINGS

The appended drawings illustrate examples and are, therefore, exemplary embodiments and not considered to be limiting in scope.

3

Figure 9:
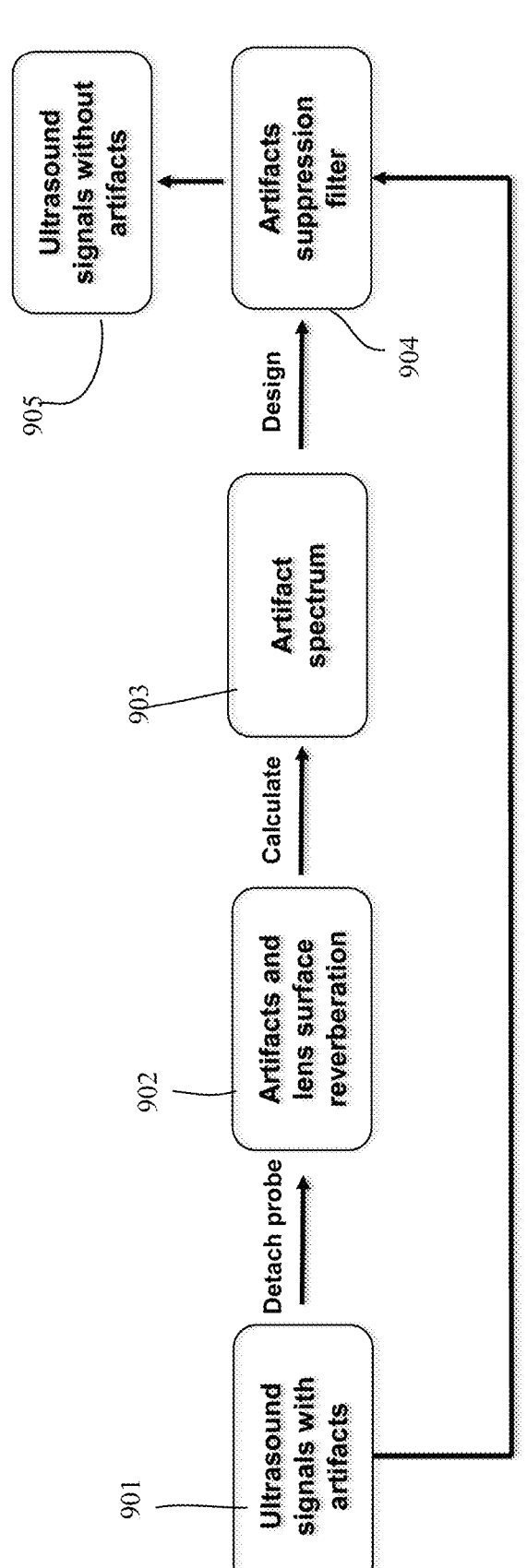

FIG. 9 depicts a block diagram illustrating a "detach probe from target" method to separate artifacts from ultrasound signals according to some embodiments.

FIG. 10 depicts a view showing an ultrasound image generated by an ultrasound system before detaching the probe from a target and an ultrasound image generated by the ultrasound system after detaching the probe from the target according to some embodiments.

Figure 11:
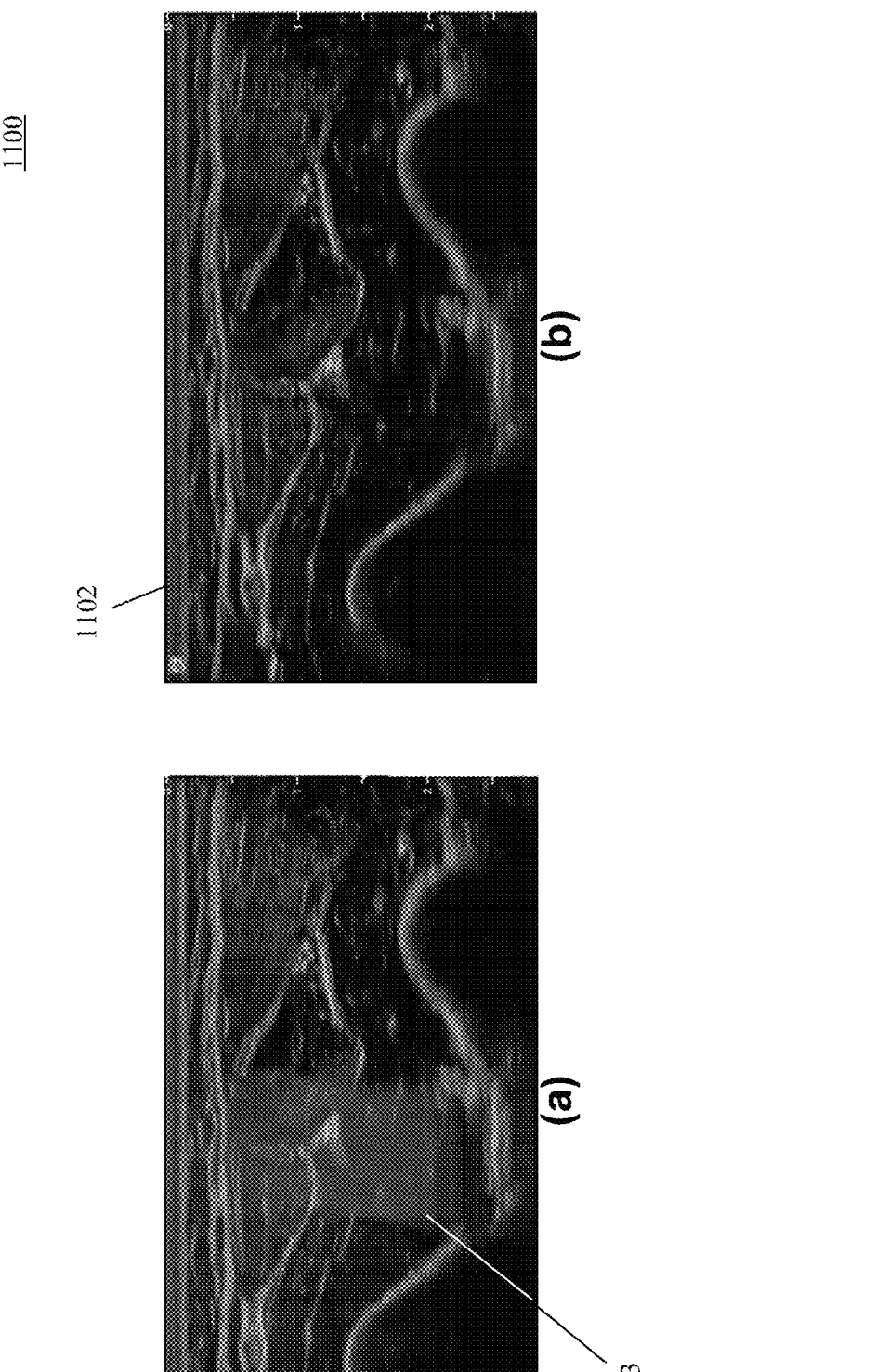

FIG. 11 shows a view illustrating an example of applying an artifacts suppression filter according to some embodiments.

Figure 12:
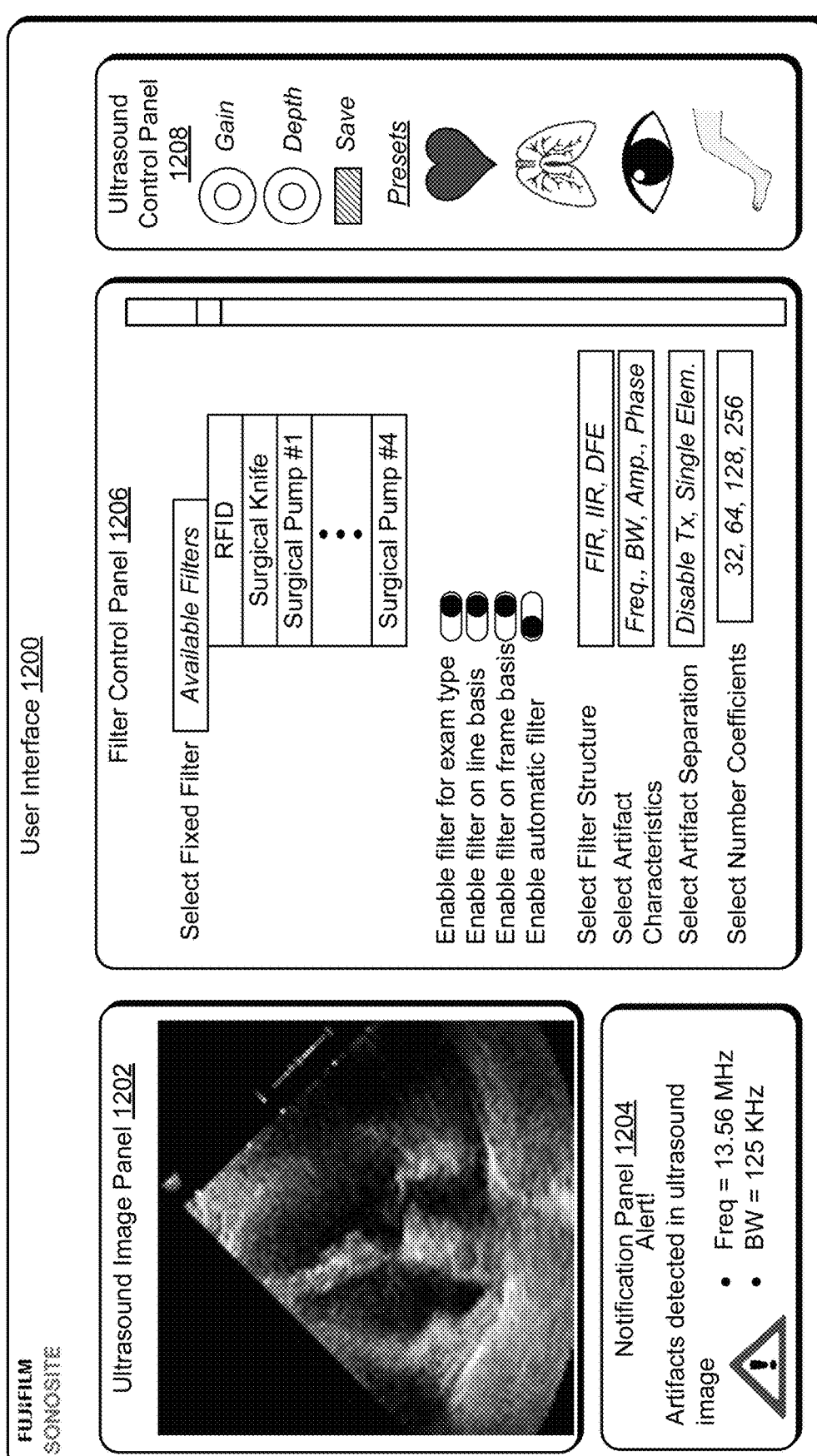

FIG. 12 illustrates an example of a user interface to control an artifact suppression filter according to some embodiments.

FIG. 13 illustrates an example method that can be implemented by an ultrasound system for suppressing artifacts with a filter in ultrasound images according to some embodiments.

FIG. 14 illustrates an example method that can be implemented by an ultrasound system for suppressing artifacts with a filter in ultrasound images according to some embodiments.

FIG. 15 illustrates an example method that can be implemented by an ultrasound system for suppressing artifacts with a filter in ultrasound images according to some embodiments.

Figure 16:
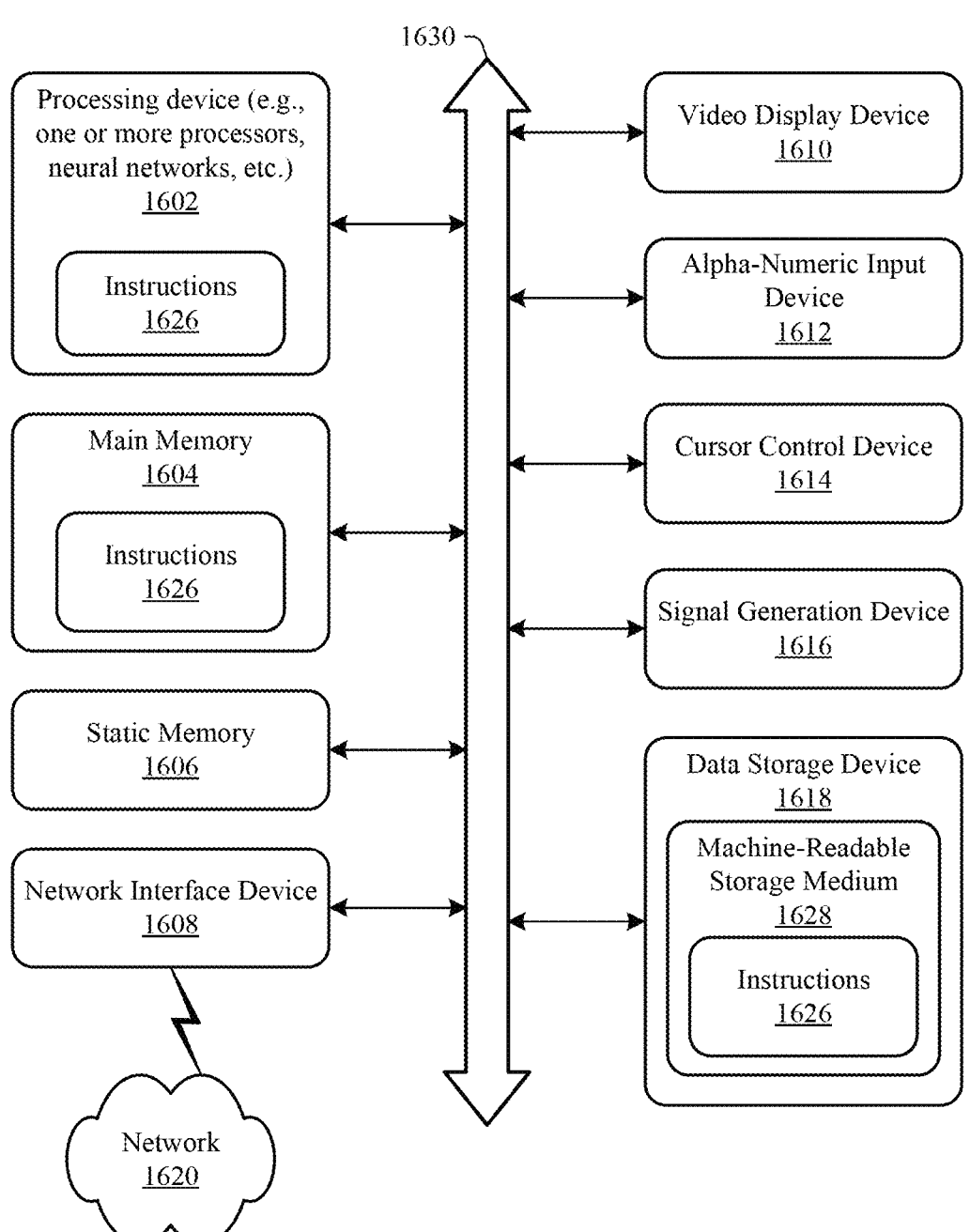

FIG. 16 illustrates a block diagram of an example computing device that can perform one or more of the operations described herein, in accordance with some embodiments.

Figure 17:
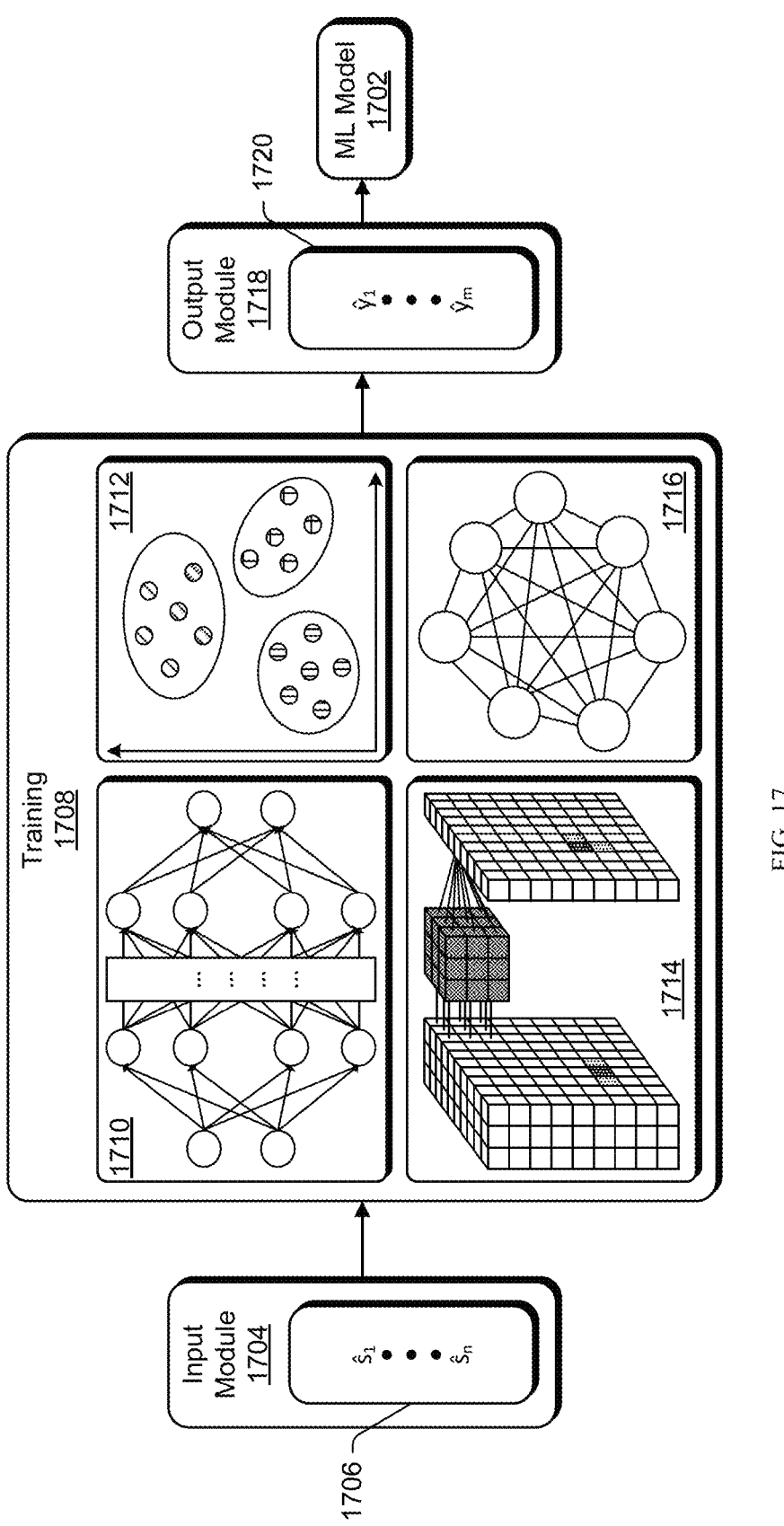

FIG. 17 illustrates an example machine-learning architecture used to train a machine-learned model in accordance with some embodiments.

Figure 18:
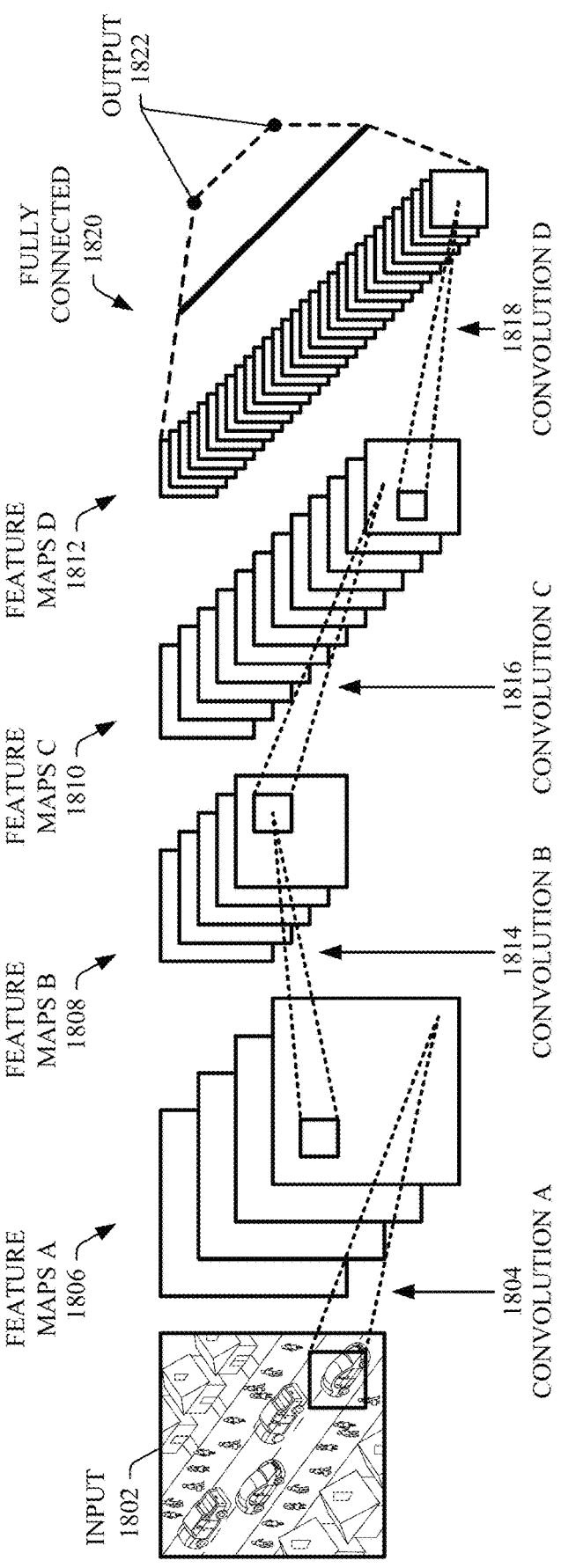

FIG. 18 illustrates an example machine-learned model using a convolutional neural network (CNN) in accordance with some embodiments.

DETAILED DESCRIPTION

In the following description, numerous details are set forth to provide a more thorough explanation of the embodiments of the present invention. It will be apparent, however, to one skilled in the art, that the embodiments of the present invention may be practiced without these specific details. In other instances, well-known structures and devices are shown in block diagram form, rather than in detail, in order to avoid obscuring the embodiments of present invention.

Conventional ultrasound systems do not have filters to effectively mitigate the artifacts caused by an interferer during ultrasound imaging. Generally, mitigating the artifacts for ultrasound imaging is challenging due to a plurality of reasons. As the artifacts frequency can overlap with the frequency of the true ultrasound signal, suppressing artifacts while keeping the ultrasound signal intact can be very difficult and result in poor imaging results. Furthermore, the artifact strength may not be constant, even for the same radiation source (e.g., interferer). For instance, depending on the operation mode of the radiation source, the artifact strength and/or frequency content can vary with time. Therefore, a traditional fixed cut-off filter will generally not result in acceptable image quality.

Furthermore, multiple positions of the ultrasound systems can be susceptible to outside radiation sources, and thus artifacts in ultrasound images can easily and often result. For example, the transducer head, cables, connectors from transducer to the system, display, and the main board can generate artifacts induced by an outside (e.g., external to the ultrasound system) interferer. In these cases, simply improving shielding on one or more parts of the ultrasound system will usually not prevent the artifacts from being generated. This problem is exacerbated since the artifact characteristics are also changing from time to time and from different devices.

1. Principle and Flowchart

Figure 1:
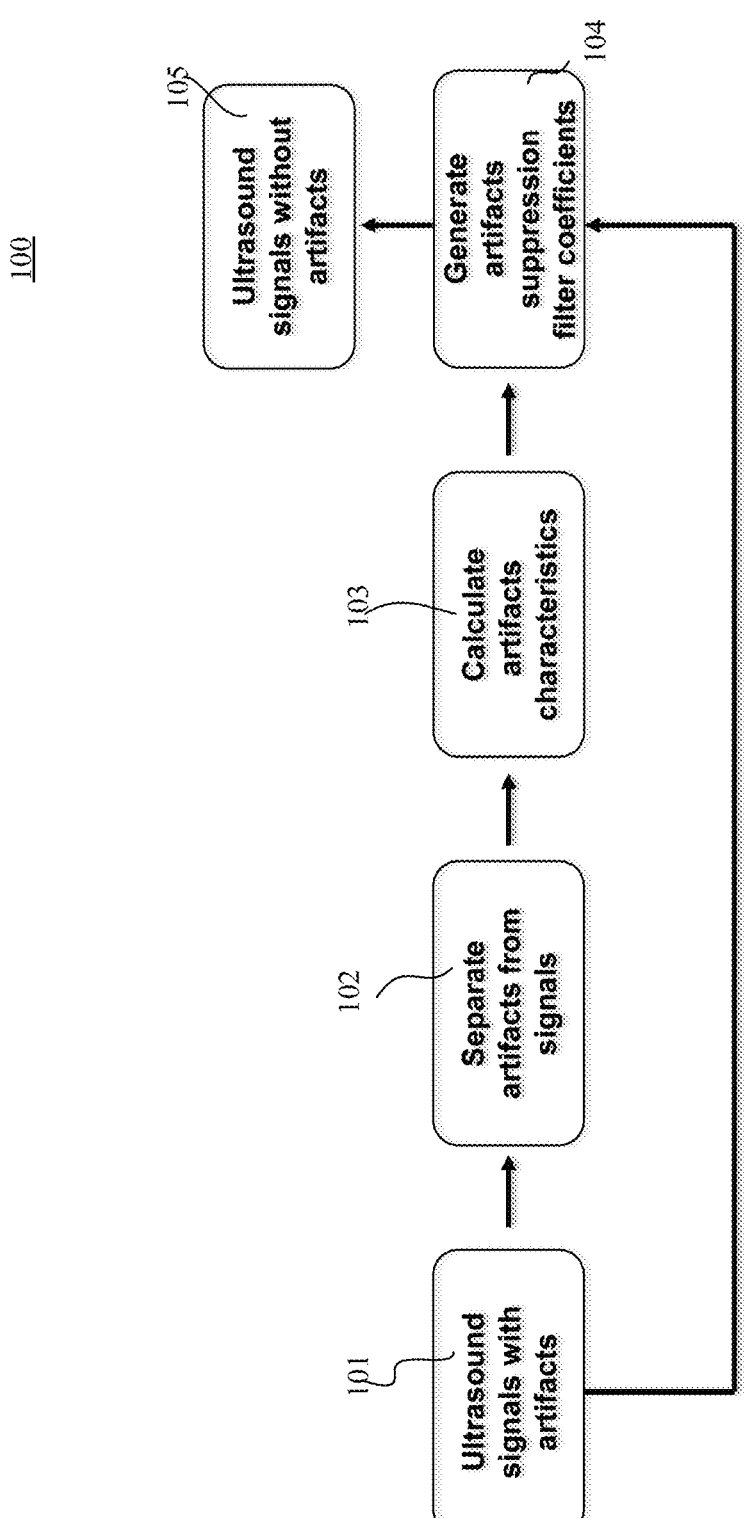
FIG. 1 depicts a block diagram illustrating an artifacts suppression filter design workflow according to some embodiments.

FIG. 1 depicts a block diagram 100 illustrating an artifacts suppression filter design workflow according to some embodiments. Operations of the workflow are performed by processing logic that can comprise hardware (circuitry, dedicated logic, etc.), software (such as is run on a general-purpose computer system or a dedicated machine), firmware, or combinations thereof. The processing logic can be included in an ultrasound system. To address an existing artifacts issue, an adaptive filter is implemented to suppress the artifacts induced from an interferer while minimizing the impact to the actual ultrasound signals that are reflected from a patient anatomy. To determine the adaptive filter, the signatures of the artifacts are analyzed in the received signals that include ultrasound signals and artifacts to separate the artifacts from the ultrasound signals. Then the characteristics of the artifacts are determined, including one or more of the artifacts frequency, bandwidth, and amplitude. Then a filter is designed (e.g., the filter structure is determined, and the filter coefficients are generated) based on the characteristics of the artifacts. The filter is applied to the received signals to output clean ultrasound signals, as described in further detail below.

In some embodiments, the artifacts suppression filter design workflow is performed by an ultrasound system that includes an ultrasound scanner configured to transmit ultrasound at a target patient anatomy and receive reflections of the ultrasound from the target patient anatomy. In some embodiments, the ultrasound scanner is an ultrasound probe, a transducer, or other ultrasound scanner. The ultrasound system can include an ultrasound machine configured to generate received data including ultrasound data based on the reflections of the ultrasound and artifact data based on an interferer. The ultrasound system can include a processor system that is implemented to determine an artifact signal that is based on the interferer, and determine, based on the artifact signal, artifact characteristics. In some embodiments, the artifact characteristics include one or more of an amplitude, a phase, a center frequency, and a bandwidth. The processor system is implemented to generate, based on the artifact characteristics, filter coefficients, and filter, based on the filter coefficients, the received data to suppress the artifact data and recover the ultrasound data.

In some embodiments, determining the artifact signal includes to instruct the ultrasound scanner to cease the transmission of the ultrasound. Additionally or alternatively, determining the artifact signal can include to instruct the ultrasound machine to reduce a system gain. Additionally or alternatively, determining the artifact signal can include enabling at least one transducer element of the ultrasound scanner for reception while the transmission is ceased. In an example, the processor system is implemented to determine a control signal, and repeat, based on the control signal, the instruction to cease the transmission of the ultrasound and to enable the at least one transducer element for the reception.

In some embodiments, the processor system determines the artifact signal as the received data from a single transducer element of the ultrasound scanner. In an example, the processor system determines the artifact signal as a summation of the received data from multiple transducer elements of the ultrasound scanner. In some embodiments, the processor system beamforms the received data from multiple transducer elements of the ultrasound scanner to generate a beamformed signal and determines the ultrasound data as a subtraction of the received data of a single transducer element from the ultrasound scanner from the beamformed signal.

In some embodiments, the processor system determines the artifact signal as data received from a transducer element of the ultrasound scanner that is not implemented to transmit the ultrasound. In some embodiments, the artifact signal is not based on the received data. Additionally or alternatively, the processor system can cause an instruction to be exposed for user consumption, where the instruction instructs the user to detach the ultrasound scanner from a patient having the patient anatomy. The processor system can cause the ultrasound scanner to transmit additional ultrasound and receive additional reflections, and apply a time-gating function to the additional reflections to determine the artifact signal.

In some embodiments, the ultrasound scanner transmits the ultrasound at a first frequency, and the processor system determines an artifact signal including to filter the received signal with a notch filter having a notch based on the first frequency. Additionally or alternatively, the ultrasound scanner transmits the ultrasound at a second frequency, and the processor system filters the received signal with an additional notch filter having an additional notch based on the second frequency and determines the artifact signal including to sum outputs of the notch filter and the additional notch filter.

In some embodiments, the processor system repeats the operations of determining the artifact signal, determining the artifact characteristics, generating the filter coefficients, and filtering the received data for different lines of the ultrasound making up an ultrasound image frame. Additionally or alternatively, the processor system repeats the operations of determining the artifact signal, determining the artifact characteristics, generating the filter coefficients, and filtering the received data for consecutive ultrasound image frames. In some embodiments, the processor system generates the filter coefficients based on at least one of a window function that determines a length of the filter and a sparse coefficient function that determines the filter coefficients that are set to zero, as described in further detail below.

As shown in FIG. 1, ultrasound signals reflected from a target patient anatomy and artifacts from an interferer are received at block 101. The ultrasound system includes an ultrasound machine configured to generate received data including ultrasound data based on the reflections of the ultrasound and artifact data based on an interferer. As shown in FIG. 1, the artifacts data are separated from the ultrasound signals data at block 102. The ultrasound system includes a processor system implemented to determine an artifact signal that is based on the interferer and determine, based on the artifact signal, artifact characteristics. As shown in FIG. 1, the artifacts characteristics are calculated at block 103. In some embodiments, the artifact characteristics include one or more of an amplitude, a phase, a center frequency, and a bandwidth. In some embodiments, the processor system is implemented to generate, based on the artifact characteristics, filter coefficients, and filter, based on the filter coefficients, the received data to suppress the artifact data and recover the ultrasound data As shown in FIG. 1, the artifacts suppression filter coefficients for the suppression filter for the artifacts are generated based on the artifact's characteristics at block 104.

Then, the received data are filtered based on the filter coefficients to suppress the artifact data and recover the ultrasound data to obtain the ultrasound signals substantially without the artifacts at block 105. In some embodiments, the recovered data include the ultrasound signals and a small amount of artifacts that is negligible comparing to the ultrasound signals. In some embodiments, the artifacts suppression filter coefficients are adjusted based on the characteristics of the received artifacts (e.g., the artifacts characteristics as previously mentioned) and an updated artifacts suppression filter with the adjusted artifacts suppression filter coefficients is applied to the received signals dynamically, on the fly while the ultrasound scanner is performing the ultrasound exam to display the ultrasound images substantially without artifacts. In some embodiments, suppressing interference artifacts includes active noise cancelling. In embodiments, for different artifacts and/or different ultrasound imaging mode (e.g., B-mode, M-mode, Color, Doppler mode, etc.), there are different methods that can be used at each of the blocks of FIG. 1. The details of each block are explained in the following sections.

1.1 Separate Artifacts from Ultrasound Signals

Figure 2:
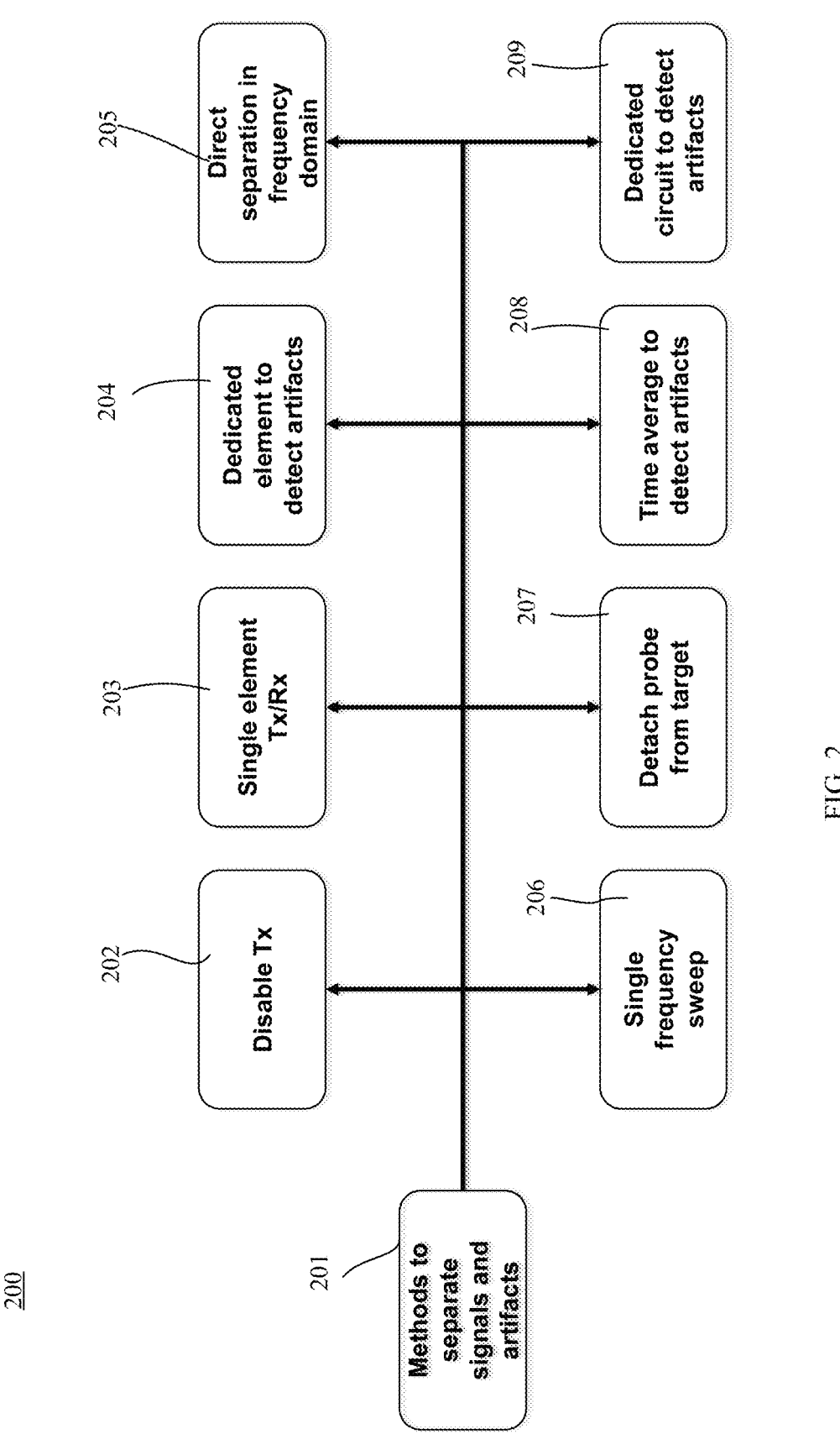
FIG. 2 illustrates a block diagram showing examples of methods to separate ultrasound signals reflected from a patient anatomy and artifacts from an interferer using an ultrasound system according to some embodiments.

FIG. 2 illustrates a block diagram 200 showing examples of methods to separate ultrasound signals reflected from a patient anatomy and artifacts from an interferer using an ultrasound system according to some embodiments. Operations of the methods are performed by processing logic that can comprise hardware (circuitry, dedicated logic, etc.), software (such as is run on a general-purpose computer system or a dedicated machine), firmware, or combinations thereof. The processing logic can be included in an ultrasound system.

As shown in FIG. 2, the methods to separate the ultrasound signals and the artifacts 201 can include one or more of a disable transmit method ("Disable Tx") 202, a single element transmit/receive method ("Single element Tx/Rx") 203, a dedicated element to detect artifacts method ("Dedicated element to detect artifacts") 204, a direct separation in frequency domain method ("Direct separation in frequency domain") 205, a single frequency sweep method ("Single frequency sweep") 206, a method that involves detaching a probe from a target ("Detach probe from target") 207, a method that uses time averaging to detect artifacts ("Time average to detect artifacts") 208 and a method that uses a dedicated circuit to detect artifacts ("Dedicated circuit to detect artifacts") 209.

In some embodiments, the "Disable Tx" method 202 includes disabling the transmit (e.g., transmission of ultrasound from the ultrasound scanner). In some embodiments, the processor system of the ultrasound system is implemented to determine an artifact signal that is based on the interferer, wherein the determine the artifact signal includes to instruct the ultrasound scanner to cease the transmission of the ultrasound. Generally, in ultrasound imaging, the system transmits ultrasound waves to a target, then receives the backscattered ultrasound signals from the target, and then forms an image based on a transmit/receive (Tx/Rx) sequence. After disabling the transmit, the ultrasound system receives only noise and artifacts (e.g., the backscattered ultrasound signals are not received). Typically, the artifacts are much larger than noise, so that the received signals can be well approximated as containing pure artifacts. In this case, the artifacts are successfully separated from actual ultrasound signals reflected from a target. As shown in Eq. (1), the total received signal after an analog-to-digital converter (ADC) can be expressed as a summation of a real ultrasound signal that carries the target object information, artifacts, and noise:

$$U(t) = S(t) + A(t) + N(t), \tag{1}$$

where t represents time, U(t) represents the total received signal, S(t) represents the real ultrasound signal reflected from a target, A(t) represents the artifacts, and N(t) represents noise. The real ultrasound signal S(t) can be expressed as a convolution of Tx, ultrasound propagation function, object function, and Rx:

$$S(t) = k \times T(t) \otimes P(t) \otimes O(t) \otimes P(t) \otimes R(t), \tag{2}$$

where k is a constant coefficient, T(t) is the transmit function, P(t) is the one-way propagation function, O(t) is the object function, and R(t) is the receive function. When the Tx is disabled, the transmit function T(t) is equal to zero, thus leading the real ultrasound signal S(t) to zero. Therefore, the received signal U(t) would be a summation of artifacts A(t) and noise term N(t), as shown in Eq. (3):

$$U(t) = A(t) + N(t). \tag{3}$$

In some embodiments, the artifacts term A(t) is much bigger than the noise N(t). Therefore, the received signal U(t) can be treated to be a very approximation of the artifacts A(t). In some embodiments, one or more system digital gains are turned down (e.g., so no amplification occurs) to reduce (or in some cases minimize) the noise term N(t) for a best approximation of the artifact signal A(t). In some embodiments, the processor system of the ultrasound system is implemented to determine an artifact signal that is based on the interferer, wherein the determine the artifact signal includes to instruct the ultrasound scanner to cease the transmission of the ultrasound and to instruct the ultrasound machine to reduce a system gain.

In some embodiments, in the "Single element Tx/Rx" method 203, the system uses a single element to transmit and receive at a time instead of using many or all the elements. Here, an element refers to a transducer element of a transducer array of the ultrasound scanner that transmits and receives ultrasound. In contrast, for true ultrasound imaging during an ultrasound examination, all or most of the received data from multiple elements are summed coherently as part of beamforming. However, this is not necessarily the case for artifacts because the artifacts don't represent a physical target and thus do not need to be beamformed. Rather, the artifacts strength would not decrease as much as true ultrasound signals in a single element case. Thus, by comparing the single element Tx/Rx data for a set of elements and the beamformed data from the set of elements, the artifacts can be separated from real ultrasound signals. In an example, the set of elements includes all the array elements of the transducer array. In another example, the set of elements includes some, but not all, of the array elements of the transducer array.

Similar to Eq. (1), received signals from a single element can be expressed as:

$$U_E(t) = S_E(t) + A_E(t) + N_E(t), \tag{4}$$

where the subscript letter "E" represents a single element. Therefore, $U_E$(t), $S_E$(t), $A_E$(t), and $N_E$(t) represent the received total signal, real ultrasound signals, artifacts, and noise from a single element, respectively. As shown in Eq. (5), the beamformed signal is a summation of all individual element signals with different delays and weights:

$$U_B(t) = \sum_E D_E(t)W_E(t)U_E(t) = \tag{5}$$
$$\sum_E D_E(t)W_E(t)(S_E(t) + A_E(t) + N_E(t)),$$

where $U_B$(t) is the beamformed signal, $D_E$(t) is a delay function for a single element, $W_E$(t) is a weight function for a single element. In a normal situation, the delay and weight function are designed so that all the element signals can add up coherently to enhance the target ultrasound strength. Meanwhile, because the artifacts usually have a direct impact on the electric board, they don't carry any information from the real target.

Therefore, for the artifacts from each element, they would add up incoherently. With the assumption that the noise contribution is small, the system can implement one or more of several different ways to separate the artifacts from real signals. In some embodiments, the artifacts are separated from real signals by directly using single element data as artifacts. For instance, the system determines the artifact signal as the data received by a single transducer element. In some embodiments, the artifacts are separated from real signals (e.g., true ultrasound signals) by simply averaging the elements data for multiple transducer elements and using the averaged result as the artifacts (e.g., the artifact signal). In an example, the averaging is performed across all of the transducer elements. In another example, the averaging is performed across some, but not all, of the transducer elements. For instance, the system can determine a faulty element and omit the data from this faulty element when averaging. This averaging approach is equivalent to applying a uniform delay and weight to the elements. In some embodiments, the artifacts are separated from real signals by subtracting the beamformed data from single element data. The subtracted result can be treated as the real ultrasound signals (e.g., the ultrasound data).

In some embodiments, in the "Dedicated element to detect artifacts" method 204, a specific element is used to detect artifacts. Like in the "Disable Tx" method 202, the Tx can be disabled for this element during the regular ultrasound scanning and only allow operation in Rx to detect artifacts. The mathematical expression for the "Dedicated element to detect artifacts" method 204 would be the same as for the "Disable Tx" method 202. The "Dedicated element to detect artifacts" method 204 is different from the "Disable Tx" method 202 in that, this element would be on (e.g., active or enabled for transmission and/or reception) from time to time following a pre-defined sequence (e.g., according to a control signal) during the entire ultrasound imaging process to monitor any potential artifacts. Any signals received by this element would be treated as artifacts.

In some embodiments, the "Direct separation in frequency domain" method 205 is enabled when the artifacts frequency is outside of the transducer frequency range. For example, for a transducer with an ultrasound frequency from about 1 to about 5 MHz, the detected signals should be located within this range. If the data contains a frequency content beyond the transducer frequency range, e.g., around 10 MHz, these data would be from artifacts. Note that harmonic signals can be removed or suppressed, such as from reducing transmit power or using pulse inversion, so that the harmonic signals are not confused with artifacts that have frequency content beyond the transducer frequency range. Therefore, a filter can be applied to separate any artifacts beyond the transducer frequency range. As shown in Eq. (6), the total received signal can be expressed in frequency domain as a summation of a real ultrasound signal that carries the object information, artifacts, and noise:

$$U(f) = S(f) + A(f) + N(f), \qquad (6)$$

where f represents frequency, U(f) represents the total received signal, S(f) represents the real ultrasound signal from target, A(f) represents the artifacts, and N(f) represents noise. For example, for a transducer with a frequency range between 1 and 5 MHz, and an artifact around 10 MHz, one can apply a low pass filter F(f) with a cut-off around 8 MHz to the total signal U(f):

$$Out(f) = \qquad (7)$$
$$F(f) \times U(f) = F(f) \times (S(f) + A(f) + N(f)) = F(f) \times (S(f) + N(f)),$$

where Out(f) is the output signal after applying the low pass filter F(f). In some embodiments, because noise N(f) is relatively small, its contribution can be neglected. Eq. (7) shows the equation of applying a low pass filter to the input total signals, which generate the real ultrasound signal S(f). At the same time, if one wants to remove the real ultrasound signal S(f) and only maintain the artifacts A(f), one can design and apply a high pass filter. In this case, the output signal Out(f) mainly includes the artifacts, which can be used for filter design in the next step.

In some embodiments, in "Single frequency sweep" method 206, the system performs a single frequency Tx/Rx sweep to identify any potential artifacts. For real (e.g., true) ultrasound signals in a continuous wave mode, the received signal frequency should be the same as the transmit signal frequency for a static target. For a static target, if the received signals include frequencies that are different from the transmit signal frequency, the received signals with those frequencies are from artifacts. "Single frequency sweep" method 206 is similar to the "Direct separation in frequency domain" method, which aims to separate the artifacts from real signals (e.g., true ultrasound signals) in the frequency domain. However, "Single frequency sweep" method 206 can also deal with the situation where the frequency band of the artifacts falls within the real ultrasound signals. By artificially creating a series of narrowband real ultrasound signals, one can locate the out-band artifacts. As shown in Eq. (8), for a single frequency, the total signal U($f_i$) is a summation of a single frequency ultrasound signal S($f_i$), artifacts A(f), and noise N(f):

$$U(f_i) = S(f_i) + A(f) + N(f), \qquad (8)$$

where $f_i$ denotes a single frequency. By applying a matched notch filter (e.g., notch filter with notch matched in frequency to the single frequency ultrasound signal) to the above total signal U(f), one can remove the single frequency ultrasound signal S($f_i$), as shown in Eq. (9):

$$Out(f_i) = \qquad (9)$$
$$F(f_i) \times U(f_i) = F(f_i) \times (S(f_i) + A(f) + N(f)) = F(f_i) \times (A(f) + N(f)),$$

By sweeping the frequency across all the transducer frequency range and adding all the results together, one can have the artifacts A(f) separated:

$$Out(f) = \sum_{f_i} Out(f_i) = \sum_{f_i} F(f_i) \times (A(f) + N(f)), \qquad (10)$$

where Out(f) is the final summed result from all the swept frequencies. Note that in some cases, one doesn't have to sweep all the frequencies. A single frequency or a portion of the frequency sweeping can be good enough to separate the artifacts from the real signals. For example, an interferer can be known to induce artifacts in certain frequencies, which can be used to determine the frequencies to sweep, so that the entire frequency band of the ultrasound signal does not need to be swept.

In some embodiments, in "Detach probe from target" method 207, the users would be requested to detach the probe from the target. In this case, because the probe does not contact with any target, the received signals should only include probe lens surface signals and their reverberations. At deeper depths (e.g., deeper than 1 or 2 cm depending on different transducers), there should be no signals at all. If there are still some signals in the data, they should all come from artifacts. Similar to the "Disable Tx" method 202, the method aims to remove the real ultrasound signals term S(t) in Eq. (1), and thus separate out the artifacts term A(f). When the probe is detached from the target, the real ultrasound signals S(t) would only contain the probe lens surface signals and their reverberations. Those signals are usually at shallow regions and correspond to the short time region in the time domain expression. Thus, if a step function (or any suitable time-gating function) is applied to the time domain signals U(t), in some embodiments, the artifacts can be extracted, as shown in Eq. (11):

$$Out(t) = H(t_i)U(t) = H(t_i) \times (S(t) + A(t) + N(t)) = A(t_i) + N(t_i), \qquad (11)$$

where Out(t) is the output signals after applying the Heaviside step function H($t_i$), $t_i$ is the time where the reverberations go away, A($t_i$) is the artifacts after time $t_i$, and N($t_i$) is the noise after time $t_i$. After applying the step function, the output signals will only contain artifacts A($t_i$) and noise N($t_i$).

In an example, the ultrasound system includes a database that maintains calibration data for different ultrasound probes. For example, the calibration data can include data indicative of probe lens surface signals and their reverberations for different ultrasound scanners and frequencies of operation. The artifact signal can be recovered from the ultrasound signal generated when the probe is detached from the target, such as via a subtraction of the calibration signal from the ultrasound signal to recover the artifacts term A(f).

In some embodiments, the "Time average to detect artifacts" method 208 takes advantage of the time-varying nature of the artifacts, while the real ultrasound signals are constant for a static target. In this case, averaging signals across multiple frames can effectively reduce or even eliminate the artifacts. The averaged signals will mainly be from real ultrasound signals. Therefore, one can separate the artifacts from real ultrasound signals, and then essentially extract the characteristics of the artifacts. As shown in Eq. (12), the averaged signals are expressed as the sum of several individual frames:

$$\text{Out}(t) = \sum_{M} U(t) = \sum_{M} (S(t) + A(t) + N(t)), \quad (12)$$

where M is the number of frames to average. Because in this case, A(t) is changing among different frames while S(t) is static, subtracting the averaged frame and a single frame scaled by M will result in mainly the artifacts:

$$\text{Out}(t) - M \times U(t) = \sum_{M} (S(t) + A(t) + N(t)) - M \times \left( \frac{S(t) + A(t) +}{N(t)} \right) = \quad (13)$$

$$\sum_{M} (A(t) + N(t)) - M \times (A(t) + N(t)),$$

In some embodiments, in "Dedicated circuit to detect artifacts" method 209, the circuit would be not used to receive and detect real ultrasound signals. Instead, it would be used only for detecting artifacts from surrounding environment. In this case, because the circuit is not part of an ultrasound receiving path, any signals detected by this circuit would be treated as artifacts to guide the subsequent filter design. Examples of a dedicated circuit to detect artifacts include RF sensing circuits and direct detectors as described in U.S. patent application Ser. No. 17/737,746 filed May 5, 2022 entitled "Detecting Electromagnetic Emissions on Ultrasound Systems" to Aliakbari et al., the disclosure of which is incorporated herein in its entirety.

1.2 Calculate Artifacts Characteristics

Figure 3:
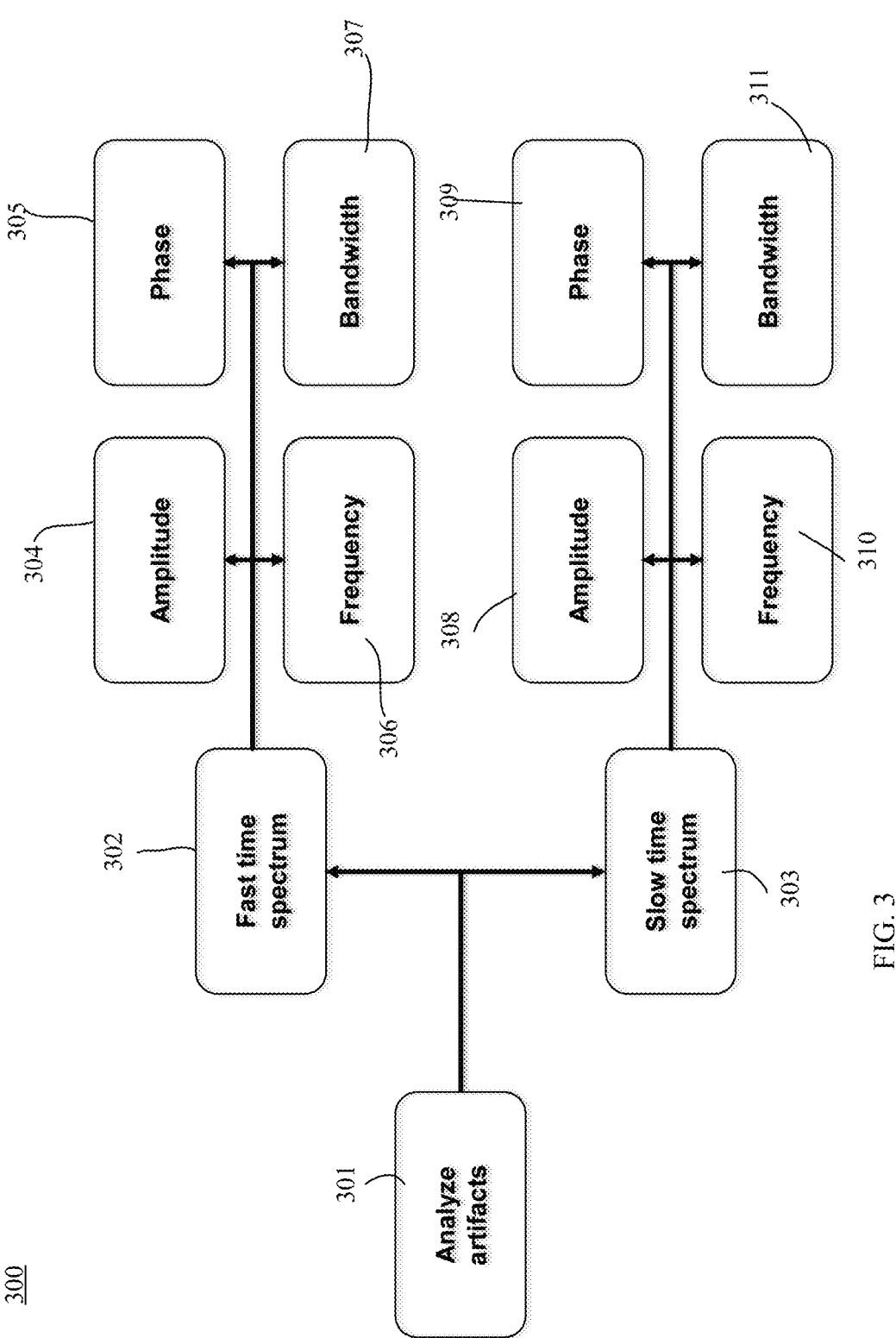
FIG. 3 depicts a block diagram that illustrates analyzing artifacts by an ultrasound system according to some embodiments.

FIG. 3 shows a block diagram 300 that illustrates analyzing artifacts by an ultrasound system according to some embodiments. After the artifacts are separated from the real ultrasound signals, the artifacts are analyzed 301 to determine their corresponding characteristics. As shown in FIG. 3, the artifacts characteristics are analyzed both in a fast time spectrum 302 and a slow time spectrum 303. For each of the fast time spectrum and the slow time spectrum, the following artifact characteristics can be analyzed and used to guide the filter design: an amplitude, a phase, a center frequency, and a bandwidth. The artifact characteristics can represent features (e.g., amplitude, phase, center frequency, bandwidth, and the like) of the artifact signal that corrupts the received ultrasound signal. Additionally or alternatively, the artifact characteristics can represent features (e.g., amplitude, phase, center frequency, bandwidth, and the like) of an interferer (e.g., an RF radiator such as an RFID device) that induces the artifact signal that corrupts the received signal. In one example, the system determines an artifact characteristic for an interferer, such as a frequency of the interferer, and changes a property of the ultrasound system, such as an ADC sampling frequency or an ultrasound frequency. For instance, by changing a frequency of the ultrasound system, the artifact frequency can be pushed out of band, and/or have a reduced amplitude. The suppression filter can be designed for the revised frequency of the ultrasound system (e.g., the new ADC or ultrasound frequency), resulting in better suppression compared to the original frequency used.

As shown in FIG. 3, an amplitude 304, a phase 305, a frequency 306 and a bandwidth 307 of one or more artifacts are analyzed in the fast time spectrum 302. As shown in FIG. 3, an amplitude 308, a phase 309, a frequency 310 and a bandwidth 311 of one or more artifacts are analyzed for the slow time spectrum 303. In some embodiments, the fast time refers to a time interval during each acquisition on a single line along a depth direction. In some embodiments, the slow time refers to a time interval between different lines.

In some embodiments, such as for B-mode and M-mode images in ultrasound, the fast time analysis is used because the images are formed line by line. In some embodiments, e.g., in B-mode and M-mode images, an absolute amplitude strength of the artifacts is determined for each line. In some embodiments, e.g., in B-mode and M-mode images, the phase shifts of the artifacts among different lines are not as important as an absolute amplitude strength of the artifacts. Thus, for the B-mode and M-mode images, a filter applied along the fast time direction can be sufficient to suppress the artifacts.

In some embodiments, such as for a Color mode and Doppler mode images, the flow information is extracted by comparing the small phase shifts among different lines. Therefore, for the Color and Doppler modes it can be harder to remove the impact from the artifacts than for the B-mode and M-mode images. In some embodiments, e.g., for a Color mode and Doppler mode images, the artifacts characteristics are extracted in both fast time and slow time domains. In some embodiments, based on the artifact's properties in both the single line direction and between the different lines direction, two filters are designed and used to suppress the artifacts.

In some embodiments, the artifacts characteristics are calculated, and one or more filters designed based on the artifacts characteristics can be applied line by line for more accuracy. In some embodiments, the artifacts characteristics are calculated and implemented frame by frame. In some embodiments, an imaging mode is determined, and based on the determined imaging mode, the filter is applied on a line basis and/or a frame basis. For example, if the imaging mode corresponds to a B-mode ultrasound image, then the filter can be applied on a frame basis. If the imaging mode corresponds to a Doppler ultrasound image, then the filter can be applied on a line basis. In some embodiments, determining the imaging mode and setting of the line versus frame filter generation and application rate is performed automatically and without user interventions.

1.3 Generate Artifacts Suppression Filter Coefficients

Figures 4A, 4B:
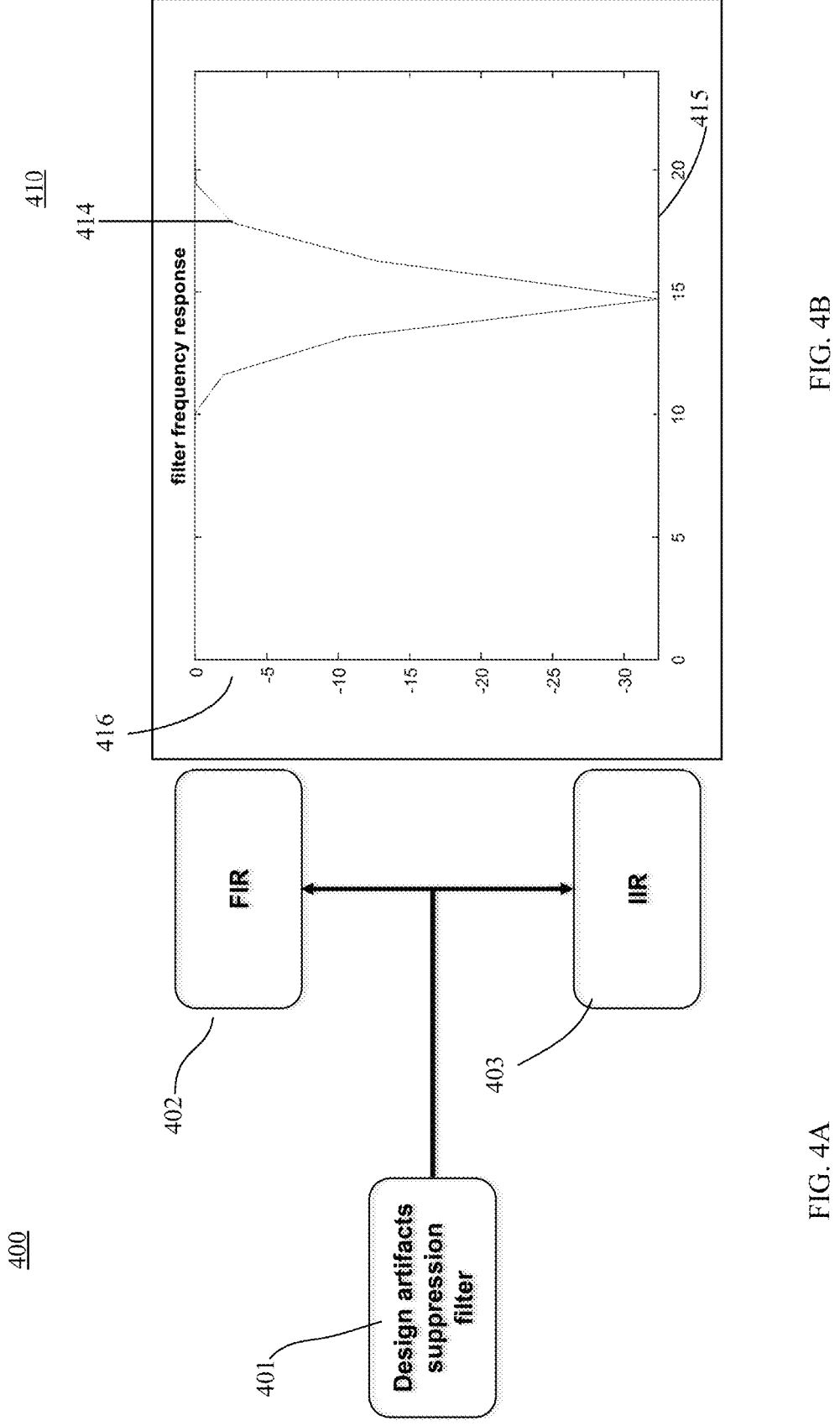
FIG. 4A depicts a view illustrating a filter design diagram according to some embodiments.
FIG. 4B shows a graph illustrating an example frequency response for a filter to suppress artifacts with a single frequency according to some embodiments.

FIG. 4A depicts a view 400 illustrating a filter design diagram according to some embodiments. After the artifacts characteristics are determined, an artifact suppression filter is designed (block 401). The artifact suppression filter can include one or more of a Finite Impulse Response (FIR) filter, an Infinite Impulse Response (IIR) filter, a linear filter, a nonlinear filter, or other artifact suppression filter. In some embodiments, the artifacts suppression filter is designed using a corresponding filter design method. As shown in FIG. 4A, artifacts suppression filter design 401 can include a FIR filter design 402, an IIR filter design 403, a linear filter design, a non-linear filter design, or any combination thereof. Depending on the artifacts' amplitude, phase, center frequency, and bandwidth, the filters can be designed accordingly to adequately mitigate the artifacts while minimizing the impact to real signals. Designing the artifact suppression filter can include determining the filter structure (e.g., IIR, FIR, sparse, lattice, linear, non-linear, etc.) and/or determining the coefficients to be used by the filter. In an example, designing the artifact suppression filter includes bit precisions for implementing the filter.

FIG. 4B shows a graph 410 illustrating an example frequency response for a filter to suppress artifacts with a single frequency (or narrowband frequency content) according to some embodiments. The graph 410 includes a frequency response curve 414 indicating a response 416 (e.g., amplitude response) of the filter to different frequencies 415. The frequency response curve 414 corresponds to a FIR notch filter, an example of an artifact suppression filter. The system can generate an artifacts suppression filter based on one or more methods. In an example, the system (e.g., ultrasound system) generates the artifact suppression filter based on resources and limitations of the system. For instance, an ultrasound system with more memory resources and faster clock speeds than a second ultrasound system may generate a longer FIR filter with higher bit precisions than a filter generated by the second ultrasound system. Hence, the system can query its available resources based on its current configuration and imaging mode to determine what artifact suppression filter to design/generate.

Figure 5:
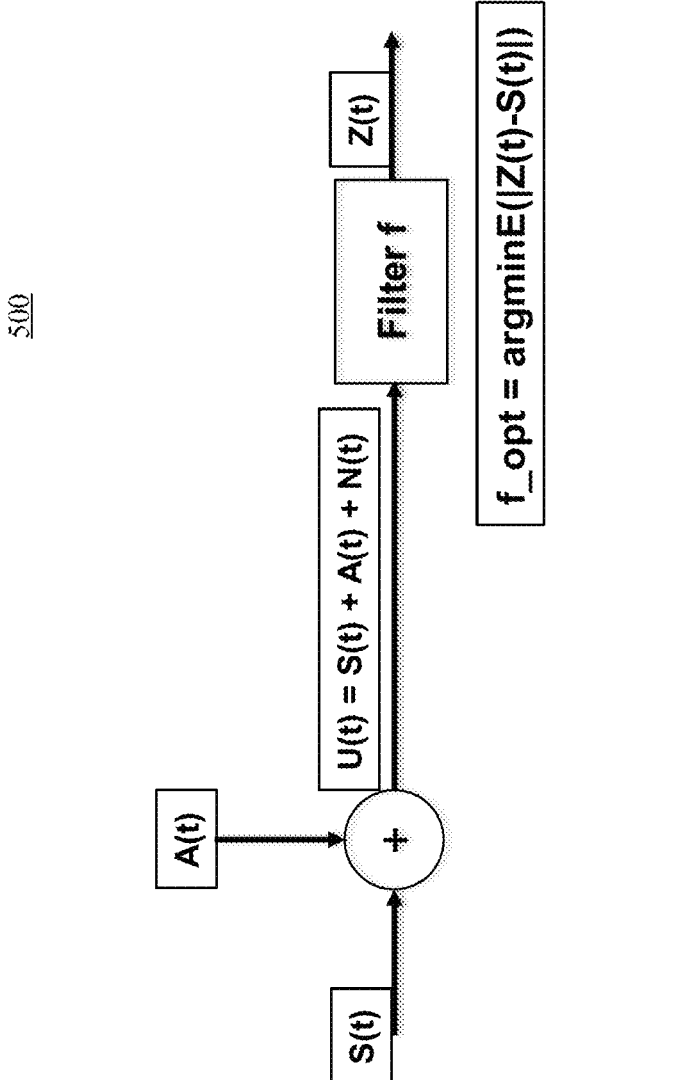
FIG. 5 shows a diagram illustrating designing a minimum error filter according to some embodiments.

FIG. 5 shows a diagram 500 illustrating designing a minimum error filter according to some embodiments. The operations to design a minimum error filter are performed by processing logic that can comprise hardware (circuitry, dedicated logic, etc.), software (such as is run on a general-purpose computer system or a dedicated machine), firmware, or combinations thereof. The processing logic can be included in an ultrasound system.

In FIG. 5, S(t) represents a real ultrasound signal, A(t) represents interference artifacts; U(t) represents system received signals comprising S(t), A(t), and noise N(t); and Z(t) represents output signals after applying an artifacts suppression filter. The optimal filter f_opt in a mean absolute error (MAE) sense can be found by calculating a minimum error arg minE(|Z(t)−S(t)|), as shown in FIG. 5. Additionally or alternatively, an optimal filter in a mean square error (MSE) sense can be found by calculating a minimum error arg minE(|Z(t)−S(t)|²).

In some embodiments, the mean absolute error (MAE) or mean square error (MSE) between the total received signals U(t) and real ultrasound signals S(t) is determined to separate real ultrasound signals from artifacts. This is equivalent to designing a filter based on the minimum MAE or MSE between the artifacts and zero. As shown in FIG. 5, an optimal filter can be found by minimizing the MAE or MSE between Z(t) and S(t). A similar approach as described in further detail below for a decision feedback equalizer (DFE), where the minimal error in a feedback loop is used to calculate filter coefficients can also be applied.

Figure 6A:
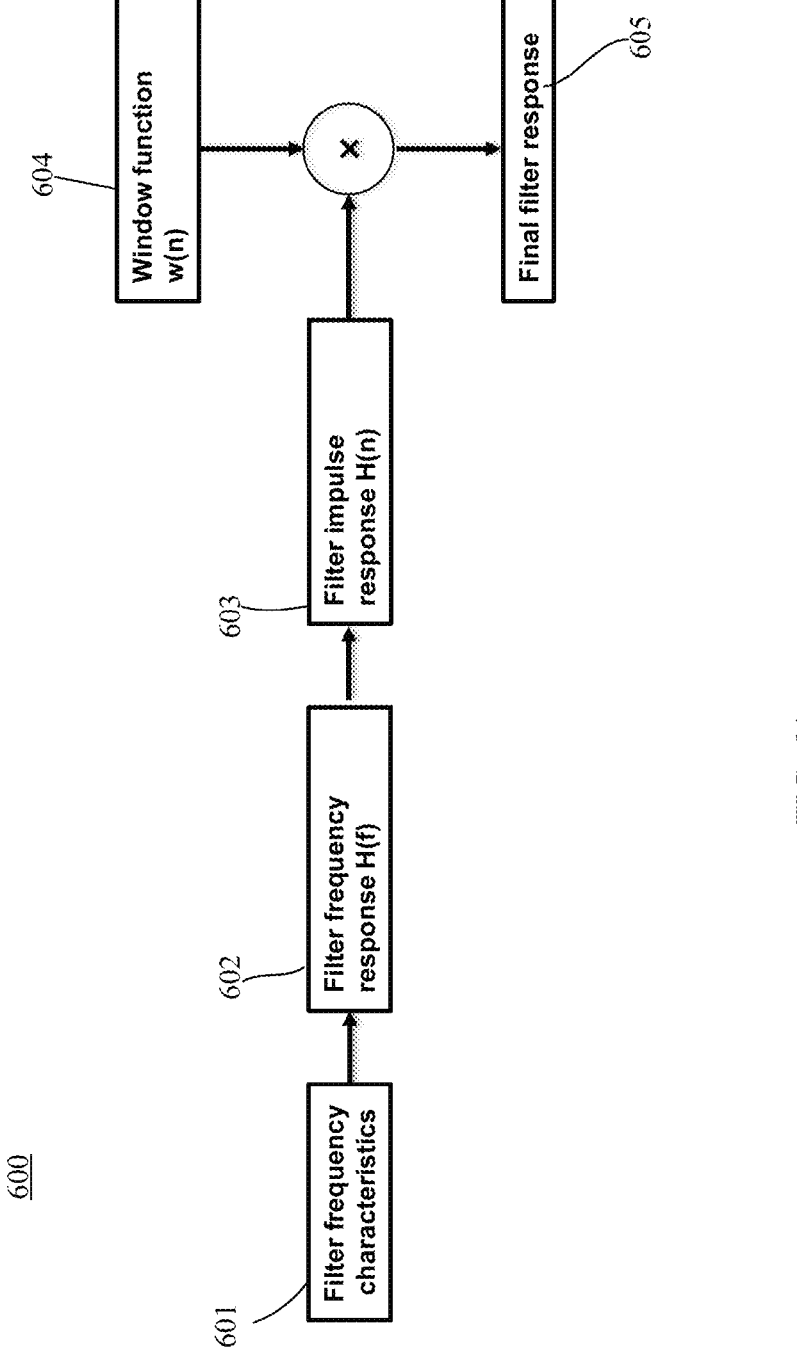
FIG. 6A shows a diagram illustrating designing a filter with a window function according to some embodiments.

FIG. 6A depicts a diagram 600 illustrating designing a filter with a window function according to some embodiments. Operations to design the filter with a window function are performed by processing logic that can comprise hardware (circuitry, dedicated logic, etc.), software (such as is run on a general-purpose computer system or a dedicated machine), firmware, or combinations thereof. The processing logic can be included in an ultrasound system.

In an implementation, there may be requirements in terms of the filter length, e.g., due to resource limitations of the system. In some embodiments, the filter frequency, bandwidth, and the number of taps (e.g., coefficients) serve as an input to design the filter. In this case, the amplitude response (or amount of filter rejection) may not be required because of the trade-off among the filter parameters. For example, in implementations, system requirements such as memory and clock speed will permit only allow a certain number of coefficients (such as 64). In this case, the desired filter rejection (such as −60 dB) may not be able to be satisfied with an FIR filter. (In embodiments, this shortcoming can be overcome by using a sparse filter which removes the constraint that non-zero filter coefficients must be contiguous, as described below in more detail.) In some embodiments, the ultrasound system can employ a filter design method, such as a window function method, to calculate the filter coefficients.

As shown in FIG. 6A, in this method, an ideal (e.g., desired) filter frequency response H(f) 602 is generated based on the desired characteristics of the filter 601, such as a cut-off frequency, passband ripples, stopband attenuations and a transition bandwidth. The ultrasound system can determine the desired filter characteristics based on the artifact characteristics. Additionally, the ultrasound system can determine the desired filter characteristics based on properties of the ultrasound system, such as ultrasound frequency, imaging mode, gain setting, etc. As shown in FIG. 6A, a suitable window function w(n) 604 is determined based on the desired trade-off between frequency responses characteristics and time-domain properties (e.g., a trade-off between the filter passband ripples and a transition bandwidth of the filter, or other trade-off). In some embodiments, the window length is determined based on the desired frequency response and the practical limit (e.g., a number of taps of the filter, or other practical limit, e.g., due to resource limitations of the ultrasound system). In some embodiments, an ideal filter impulse response in time domain H(n) 603 is generated based on the desired frequency response H(f) 602. In some embodiments, the ideal filter impulse response in time domain H(n) 603 is generated by taking an inverse transform (e.g., an inverse Fourier transform) of the desired frequency response. Then, the window function w(n) 604 is applied to shape the frequency responses and control sidelobe levels to output a final filter response at block 605. In some embodiments, other filter design methods can also be used, including but not limited to a Butterworth IIR filter, a Chebyshev type I IIR filter, Chebyshev type II IIR filter, constrained least squares method, elliptic IIR filter, Parks-McClellan filter design algorithm, frequency response sampling, Kaiser window method, and the like.

In an example, a sparse coefficient function can be used to design the filter. The sparse coefficient function can determine which filter coefficients are set to zero, to reduce computational resources and latency needed to implement the filter. For instance, the filter can have a time span corresponding to R coefficients, and the sparse coefficient function can determine that only P of the coefficients are non-zero valued and set the other R-P coefficients to zero (R>P) for integers R and P. In an example, the sparse coefficient function can set a coefficient to zero if its magnitude is below a threshold magnitude. In another example, the sparse coefficient function can exploit the artifacts characteristics, such as a center frequency, to determine the positions of coefficients needed in the filter, such as every third coefficient, a group of five coefficients surrounding every $20^{th}$ coefficient, etc., based on the center frequency. In some embodiments, some positions of coefficients needed in the filter are determined based on the characteristics of the artifacts. In some embodiments, coefficients for other positions of the filter can be set to zero by the sparse coefficient function.

Figure 6B:
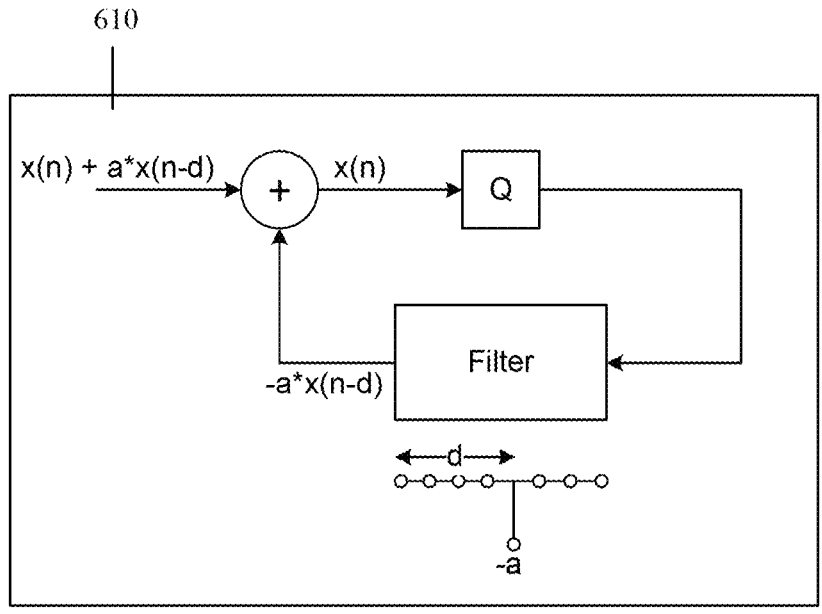
FIG. 6B shows a diagram illustrating a decision feedback filter according to some embodiments.

FIG. 6B shows a diagram illustrating a decision feedback filter according to some embodiments. Operations of the decision feedback filter are performed by processing logic that can comprise hardware (circuitry, dedicated logic, etc.), software (such as is run on a general-purpose computer system or a dedicated machine), firmware, or combinations thereof. The processing logic can be included in an ultrasound system.

In some embodiments, the ultrasound system can implement a decision feedback equalizer (DFE) as an artifact suppression filter 610. The DFE includes a filter in a feedback loop configuration, and the feedback loop also includes a nonlinearity labeled "Q". When the feedback filter is set with coefficients having weights and delays matching reflections in the input signals (e.g., the received ultrasound signal), the output of the DFE additively cancels the reflections and perfectly recovers the signal x(n), as shown in FIG. 6B.

In some embodiments, the filter coefficients can be determined via an adaptive rule (e.g., a stochastic gradient descent rule), such as:

Least Mean Square $(LMS)$: $f(n+1) = f(n) + mu \times r \times [x(n) - s(n)]$

Decision Driven $(DD)$-$LMS$: $f(n+1) = f(n) + mu \times r \times [x(n) - Q\{x(n)\}]$ for vector r containing input samples to the feedback filter, where updating of the vector of the filter coefficients f is in time domain and n indicates time, mu represents a step size (e.g., a small number that is about 0.01), s(n) denotes a source signal (e.g., an ultrasound signal generated as a reflection from a patient anatomy that does not include artifacts from an interferer), and x(n) is the DFE output that attempts to reconstruct the source signal s(n), as illustrated in FIG. 6B. To operate on an ultrasound image, the nonlinear function Q can include a binary output with values corresponding to colors of black and white. That is, the nonlinearity Q can be a nearest value decision device that maps its input sample to a value corresponding to black or a value corresponding to white. Since the source signal s(n) is not generally known for ultrasound signals, it can be generated by insertion of an extra line of data when generating the ultrasound data, as described with regards to FIG. 6C.

Figure 6C:
FIG. 6C shows a view illustrating an extra line of pixels embedded into ultrasound image data and used to determine coefficients of a decision feedback filter according to some embodiments.

FIG. 6C is a view 620 illustrating an extra line of pixels 621 embedded into the ultrasound image data and used to determine coefficients of a decision feedback filter according to some embodiments. In some embodiments, the extra line of pixels 621 embedded into the ultrasound image data are not displayed on a display device. To make correct decisions, the coefficient adjustment of the filter of the DFE can be performed on data embedded into the ultrasound image that contains true black and white samples, as illustrated in

16

FIG. 6B. To embed these data into the ultrasound image, the ultrasound system can provide excitation signals to the ultrasound probe to generate the black and white samples. If the embedded samples are then corrupted by an interferer when they are converted to received ultrasound data, then the pattern (e.g., extra line) in FIG. 6B will no longer be purely black and white, and the filter coefficients of the DFE can be adjusted to a setting to cancel the interference, using the DD-LMS adaptation rule described above. For true ultrasound image data (e.g., other than the embedded line in this example), the filter coefficients may not be adjusted. For instance, they can remain fixed. However, the coefficients can be adjusted for the extra line data on multiple image frames to determine a setting of the filter in the DFE to suppress the artifacts caused by the interferer.

EXAMPLES

Figure 7:
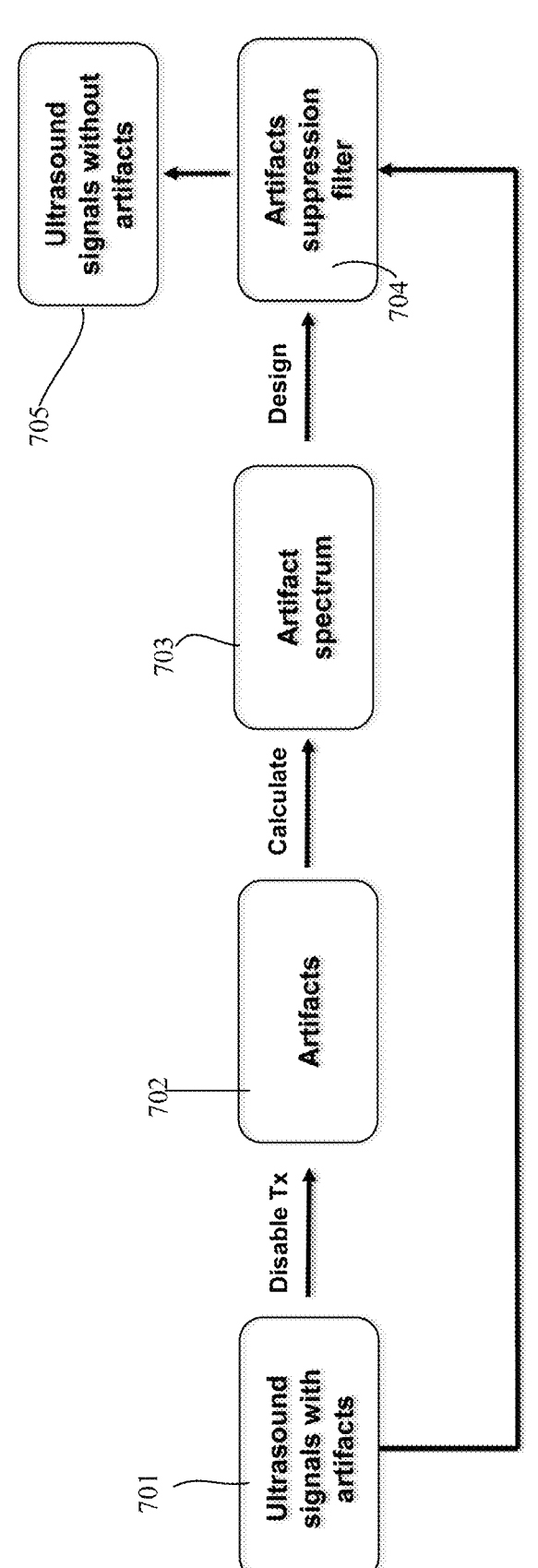
FIG. 7 depicts a block diagram illustrating a "Disable Tx" (e.g., disable transmission) method to separate signals and artifacts according to some embodiments.

2.1 Separate Artifacts from Signals—A Disable Transmit ("Disable Tx") Method FIG. 7 is a block diagram 700 illustrating a "Disable Tx" method (e.g., 202 in FIG. 2) to separate signals and artifacts according to some embodiments. Operations of the method are performed by processing logic that can comprise hardware (circuitry, dedicated logic, etc.), software (such as is run on a general-purpose computer system or a dedicated machine), firmware, or combinations thereof. The processing logic can be included in an ultrasound system. As shown in FIG. 7, the ultrasound system receives ultrasound signals with artifacts 701. After disabling transmit Tx, the system receives artifacts 702 that are substantially without ultrasound signals. In some embodiments, the system may receive artifacts 702 and a small amount of ultrasound signals that is negligible comparing to the artifacts 702.

Figure 8:
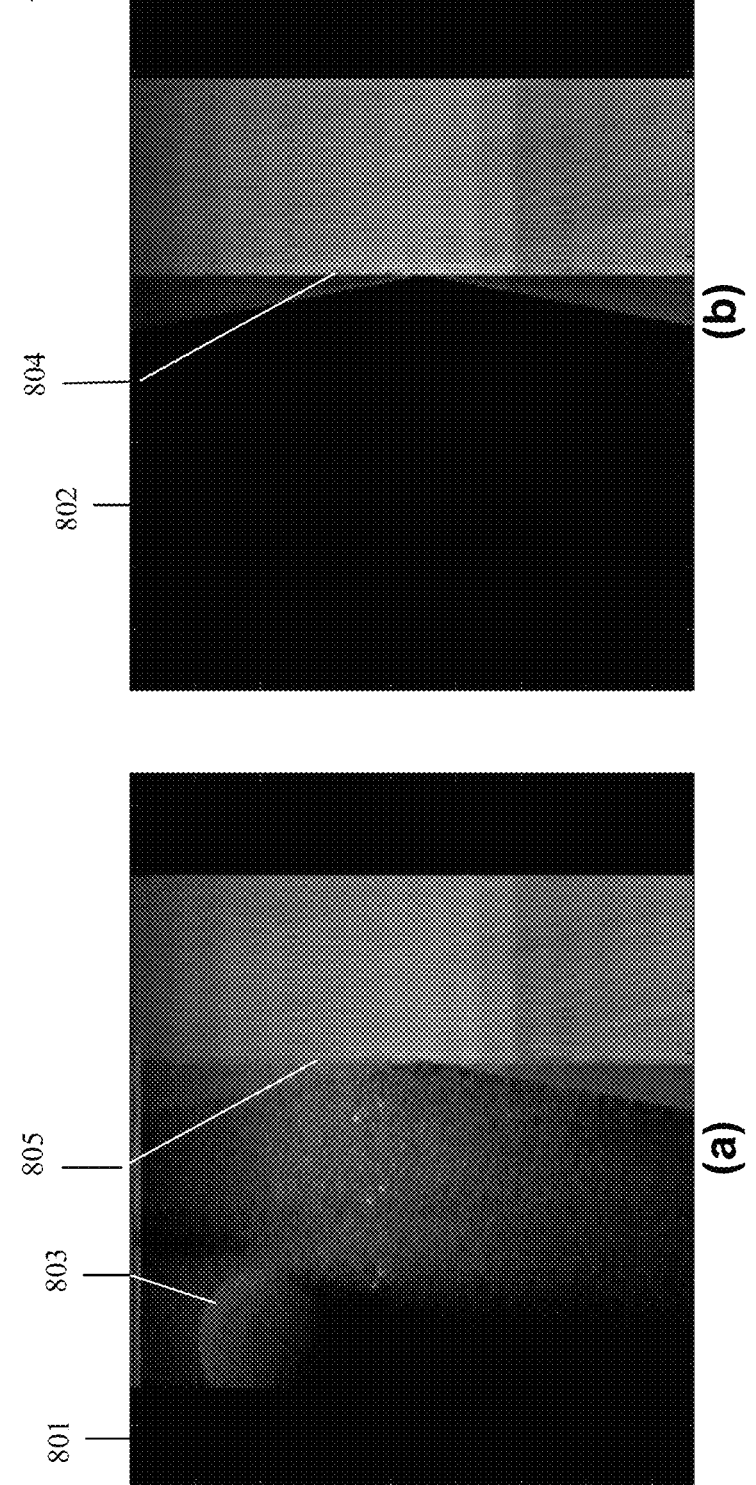
FIG. 8 depicts a view showing an ultrasound image generated by an ultrasound system before disabling Tx and an ultrasound image generated by the ultrasound system after disabling Tx according to some embodiments.

FIG. 8 depicts a view 800 showing an ultrasound image (a) 801 generated by the ultrasound system before disabling Tx and an ultrasound image (b) 802 generated by the ultrasound system after disabling Tx according to some embodiments. As shown in FIG. 8, the ultrasound image (a) 801 includes phantom images 803 generated based on the received ultrasound signals and radio frequency (RF) artifacts 805. As shown in FIG. 8, the ultrasound image (b) 802 includes only (e.g., substantially) RF artifacts 804. As shown in FIG. 8, after disabling Tx, the system only receives artifacts that significantly simplifies extracting artifacts properties/characteristics to design an artifact suppression filter. It should be noted that data in the ultrasound image (a) 801 and the ultrasound image (b) 802 were acquired at different times. Therefore, there is a slight difference between the artifacts in the images.

Returning back to FIG. 7, an artifact spectrum 703 is calculated based on the artifacts. In some embodiments, one or more artifact characteristics selected from the group consisting of an amplitude, a phase, a center frequency, and a bandwidth are calculated based on the artifacts (e.g., the artifact spectrum). As shown in FIG. 7, an artifact suppression filter 704 is designed based on the artifacts spectrum 703. In some embodiments, designing artifact suppression filter 704 includes generating the filter coefficients based on the artifact characteristics. As shown in FIG. 7, artifact suppression filter 704 is used to filter the received signals 701 to suppress the artifacts and to recover the ultrasound signals without artifacts 705.

2.2 Separate Artifacts from Signals—A "Detach Probe from Target" Method

FIG. 9 depicts a block diagram 900 illustrating a "Detach probe from target" method (e.g., 207 in FIG. 2) to separate artifacts from ultrasound signals according to some embodiments. Operations of the method are performed by processing logic that can comprise hardware (circuitry, dedicated logic, etc.), software (such as is run on a general-purpose computer system or a dedicated machine), firmware, or combinations thereof. The processing logic can be included in an ultrasound system. As discussed above, an ultrasound scanner of the ultrasound system is configured to transmit ultrasound at a target anatomy and receive reflections of the ultrasound from the target anatomy. An ultrasound system is configured to receive ultrasound signals reflected from the target anatomy with artifacts 901. As shown in FIG. 9, after detaching the scanner (e.g., a probe) from a target (e.g., the target anatomy), the system receives artifacts and lens surface reverberations 902. That is, after detaching the probe from the target, the only ultrasound signals the system receives are from a lens surface and its reverberations.

FIG. 10 is a view 1000 showing an ultrasound image (a) 1001 generated by the ultrasound system before detaching the probe from the target and an ultrasound image (b) 1002 generated by the ultrasound system after detaching the probe from the target according to some embodiments. As shown in FIG. 10, the ultrasound image (a) 1001 includes phantom images 1003 generated based on the received ultrasound signals and RF artifacts 1004. As shown in FIG. 10, the ultrasound image (b) 1002 includes only RF artifacts and lens surface reverberations 1005. As shown in FIG. 10(*b*), after detaching the probe from the target, other than the lens surface signals and its reverberations, the other signals are purely from artifacts. Therefore, one can treat these signals (from deeper depths) as artifacts, perform analysis, and design corresponding filters. It should be noted that data in the ultrasound image (a) 1001 and the ultrasound image (b) 1002 were acquired at different times. Therefore, there is a slight difference between the artifacts in the images.

Returning back to FIG. 9, an artifact spectrum 903 is calculated based on the artifacts and lens surface reverberation. In some embodiments, artifact spectrum 903 is determined by suppressing the lens surface reverberation. In some embodiments, artifacts spectrum is determined by using the deeper depths' signals, where the lens surface reverberation is minimal, and only artifacts are left. In some embodiments, the system suppresses the lens surface reverberation using calibration data that is maintained in a database. The calibration data can represent lens surface reverberation data for the ultrasound probe and frequency used to generate the ultrasound data when the probe is detached from the target. In some embodiments, artifact characteristics selected from the group consisting of an amplitude, a phase, a center frequency, and a bandwidth are calculated based on the artifacts. As shown in FIG. 9, an artifact suppression filter 904 is designed based on the artifacts spectrum 903. Additionally or alternatively, the system can determine the artifact suppression filter 904 based on the artifact characteristics. In some embodiments, designing artifact suppression filter 904 includes generating the filter coefficients based on the artifact and lens surface lens surface reverberation characteristics. As shown in FIG. 9, artifact suppression filter 904 is used to filter the received signals 901 to suppress the artifacts and to recover the ultrasound signals without artifacts 905.

2.3 Data after Applying Artifacts Suppression Filter

FIG. 11 depicts a view 1100 that illustrates an example of applying an artifacts suppression filter according to some embodiments. In some embodiments, the artifacts detection, analysis, and filter design follow the workflow, as described with respect to FIG. 1. FIG. 11 shows an ultrasound image (a) 1101 before applying an artifacts suppression filter and an ultrasound image (b) 1102 after applying the artifacts suppression filter. As shown in FIG. 11, the ultrasound image (a) 1101 includes a target anatomy with artifacts 1103 that are caused by an RFID interferer in proximity to the ultrasound system that generated the ultrasound image (a) 1101. The ultrasound image (b) 1102 includes a target anatomy without the artifacts. As one can see from FIG. 11, after applying the artifacts suppression filter, the artifacts disappear while the target anatomy image remains intact.

3. System Behaviors

FIG. 12 illustrates an example of a user interface 1200 to control an artifact suppression filter according to some embodiments. Operations to control the artifact suppression filter are performed by processing logic that can comprise hardware (circuitry, dedicated logic, etc.), software (such as is run on a general-purpose computer system or a dedicated machine), firmware, or combinations thereof. The processing logic can be included in an ultrasound system.

In embodiments, an ultrasound system includes an ultrasound scanner that transmits ultrasound at a patient anatomy and generates ultrasound data based on reflections of the ultrasound from the patient anatomy. The ultrasound system includes a processor system that determines an artifact signal that is caused by an interferer and that corrupts the ultrasound data. In some embodiments, the processor system determines, based on the artifact signal, one or more artifact characteristics selected from the group consisting of an amplitude, a phase, a center frequency, and a bandwidth. The processor system can generate, based on the artifact characteristics, filter coefficients. The processor system filters, based on the filter coefficients, the ultrasound data to suppress the corruption caused by the artifact signal. The ultrasound system includes a user interface (UI) on a display device that displays an ultrasound image based on the ultrasound data after it has been filtered. Additionally or alternatively, the processor system determines the artifact signal based on the ultrasound data.

In some embodiments, the display device displays an additional ultrasound image based on the ultrasound data before it has been filtered, and receives, via the UI, a user selection to generate the filter coefficients and filter the ultrasound data. In some embodiments, the processor system generates, responsive to the user selection, the ultrasound image. Additionally or alternatively, the processor system can implement a machine-learned model to generate, based on the ultrasound data before it has been filtered, an image quality score. The processor system can compare the image quality score to a threshold score. In some embodiments, filtering the ultrasound data is responsive to the comparison indicating the image quality score is below the threshold score, as described in further detail below.

In some embodiments, the UI design includes a system notification part and an algorithm implementation part. In some embodiments, for the system notification, the user interface provides notifications to a user including a notification indicating presence of an artifact and a suggestion on the availability of user-on-demand artifact suppression feature. In some embodiments, the algorithm implementation includes a pre-defined static filter as a default setting (user cannot control), an adaptive filter without user controls, and/or an adaptive filter as an advanced feature which a user can turn on/off.

The user interface 1200 can be displayed by any suitable device or component of an ultrasound system, such as an ultrasound probe, and an ultrasound machine, a display device, etc. As shown in FIG. 12, the user interface 1200 includes an ultrasound image panel 1202, a notification panel 1204, a filter control panel 1206, and an ultrasound control panel 1208. In some embodiments, the ultrasound image panel 1202 can display any suitable ultrasound image, such as a B-mode image, M-mode image, Doppler image, etc. The notification panel 1204 can display a notification or alert when the ultrasound system determines that an ultrasound image, such as the ultrasound image displayed in the ultrasound image panel 1202, includes artifacts caused by an interferer (e.g., a radiation source), such as an RFID reader or transmitter. In some embodiments, the ultrasound system includes a machine-learned model to automatically determine if an ultrasound image is corrupted by an interferer and contains artifacts. In some embodiments, the machine-learned model is executed responsive to an event, such as the ultrasound image being saved. The machine-learned model can generate a probability (score) that the ultrasound image contains artifacts due to an interferer. If the probability is greater than a threshold probability, such as 80%, then the ultrasound system can cause the notification panel 1204 to be displayed in the user interface 1200 and display the warning/alert. The warning can include text, an icon, an animation, an audio message, haptic feedback (e.g., the ultrasound scanner can vibrate), and the like. In some embodiments, the notification panel 1204 displays artifact characteristics, such as an amplitude, a phase, a center frequency, and/or a bandwidth about the interferer and/or artifacts caused by the interferer.

In the example in FIG. 12, the notification panel 1204 indicates that an interferer and/or artifacts are detected with a center frequency of 13.56 MHz and a bandwidth of 125 KHz. Additionally or alternatively, the notification panel 1204 can indicate a detected source type for the interferer, such as text indicating that an RFID source is responsible for the artifacts. In some embodiments, the ultrasound system can include a machine-learned model to determine the type/source of the interferer.

The filter control panel 1206 displays parameters and user-selectable control options for a filter for suppressing artifacts caused by the interferer. The filter control panel 1206 can include an option to select a fixed filter from a database of filters stored and/or accessible by the ultrasound system. In the example in FIG. 12, the available filters can be accessed via a pull-down menu with options for a filter to suppress RFID artifacts, surgical knife artifacts, artifacts caused by a surgical pump #1 (e.g., a surgical pump made by a first manufacturer), and a surgical pump #4 (e.g., a surgical pump made by another manufacturer). These filters can be determined a priori (e.g., before the ultrasound exam) for specific interferers causing known artifacts, and be maintained by the database.

The filter control panel 1206 can also include options to enable different filter selections, such as to enable a filter based on an examination type, to enable a filter on a line basis (e.g., a filter that is adapted and applied on a line-by-line basis that is suitable for a Doppler imaging). The filter enable options also can enable a filter on a frame basis (e.g., a filter that is adapted and applied on an ultrasound image frame basis that is suitable for a B-mode imaging). The filter enable options also can enable a filter automatically. For example, when this option is enabled, the ultrasound system can determine any suitable filter based on any parameter and automatically apply the filter to an ultrasound image to suppress artifacts caused by an interferer. In some embodiments, two or more of the filter enable options can be simultaneously selected. In the example in FIG. 3, the option to enable a filter for artifact suppression automatically is selected.

The filter control panel 1206 can also include options (e.g., pull-down menus) to select parameters for an artifact suppression filter. The parameter selection options include selections for a filter structure (e.g., FIR, IIR, DFE, etc.), and artifact characteristics used to determine a filter, such as a frequency and a bandwidth of an interferer and/or measured artifacts. The parameter selection options include selections for a technique used to determine an artifact signal (e.g., to separate the artifacts from ultrasound reflections), including to disable transmission, enable a single transducer element, etc., as described with respect to FIG. 2. The parameter selection options include selections for a number of coefficients in a suppression filter. Additionally or alternatively, parameter selection options can include selections for a filter length or a time span, and/or to enable a sparse filter.

The ultrasound control panel 1208 includes any suitable controls and settings for controlling the ultrasound system, such as depth and gain adjustments, and a button to store images and/or video clips. The ultrasound control panel 1208 can also include icons to select examination presets. These controls are meant to be exemplary and non-limiting.

4. Example Procedures

FIG. 13 illustrates an example method 1300 that can be implemented by an ultrasound system for suppressing artifacts with a filter in ultrasound images according to some embodiments. Operations of the method are performed by processing logic that can comprise hardware (circuitry, dedicated logic, etc.), software (such as is run on a general-purpose computer system or a dedicated machine), firmware, or combinations thereof. The processing logic can be included in an ultrasound system. The ultrasound system can include an ultrasound scanner (e.g., a transducer or probe), an ultrasound machine, a processor system, and a display device.

Ultrasound signals are transmitted at a patient anatomy and reflections of the ultrasound from the patient anatomy are received (block 1302). Received data is generated, and includes ultrasound data based on the reflections of the ultrasound and artifact data based on an interferer (block 1304). An artifact signal that is based on the interferer is determined (block 1306). Based on the artifact signal, one or more artifact characteristics are determined, the artifact characteristics selected from the group consisting of an amplitude, a phase, a center frequency, and a bandwidth (block 1308). Filter coefficients are generated based on the artifact characteristics (block 1310). The received data is filtered, based on the filter coefficients, to suppress the artifact data and recover the ultrasound data (block 1312).

In some embodiments, determining the artifact signal includes to instruct the ultrasound scanner to cease the transmission of the ultrasound. Additionally or alternatively, determining the artifact signal can include to instruct the ultrasound machine to reduce a system gain. Additionally or alternatively, determining the artifact signal can include enabling at least one transducer element of the ultrasound scanner for reception while the transmission is ceased. In some embodiments, the processor system is implemented to determine a control signal, and repeat, based on the control signal, the instruction to cease the transmission of the ultrasound and to enable the at least one transducer element for the reception.

In some embodiments, the processor system determines the artifact signal as the received data from a single transducer element of the ultrasound scanner. In an example, the processor system determines the artifact signal as a summation of the received data from multiple transducer elements of the ultrasound scanner. In some embodiments, the processor system beamforms the received data from multiple transducer elements of the ultrasound scanner to generate a beamformed signal and determines the ultrasound data as a subtraction of the beamformed signal and the received data of a single transducer element from the ultrasound scanner.

In some embodiments, the processor system determines the artifact signal as data received from a transducer element of the ultrasound scanner that is not implemented to transmit the ultrasound. Additionally or alternatively, the artifact signal may not be based on the received data. For example, the processor system can determine the artifact signal by detaching the ultrasound scanner from the patient, enabling ultrasound transmission, and determining the artifact signal by removing reflections from a lens of the ultrasound scanner. For instance, the processor system can cause an instruction to be exposed for user consumption (e.g., on a user interface of a display device), the instruction indicating to detach the ultrasound scanner from a patient having the patient anatomy. The processor system can cause the ultrasound scanner to transmit additional ultrasound and receive additional reflections (e.g., from a lens of the ultrasound scanner), and apply a time-gating function to the additional reflections to determine the artifact signal. Examples of the time-gating function include a step function, a ramp, a pulse, etc.

In some embodiments, the ultrasound scanner transmits the ultrasound at a first frequency, and the processor system determines the artifact signal including to filter the received signal with a notch filter having a notch based on the first frequency. Additionally or alternatively, the ultrasound scanner can transmit the ultrasound at a second frequency, and the processor system can filter the received signal with an additional notch filter having an additional notch based on the second frequency. The processor system can determine the artifact signal by summing outputs of the notch filter and the additional notch filter. The processor system can repeat this process for multiple frequencies of ultrasound and multiple notch filters, e.g., across the usable ultrasound bandwidth, to reconstruct the artifact signal.

In some embodiments, the processor system can repeat to determine the artifact signal, to determine the artifact characteristics, to generate the filter coefficients, and to filter the received data for different lines of the ultrasound making up an ultrasound image frame. Additionally or alternatively, the processor system can repeat the determine the artifact signal, the determine the artifact characteristics, the generate the filter coefficients, and the filter the received data for consecutive ultrasound image frames.

In some embodiments, the processor system generates the filter coefficients based on a window function that determines a length of the filter. Additionally or alternatively, the processor system can generate the filter coefficients based on a sparse coefficient function that determines the filter coefficients that are set to zero, and the positions of the zero and non-zero coefficients in the filter (e.g., in a tapped delay line).

FIG. 14 illustrates an example method 1400 that can be implemented by an ultrasound system for suppressing arti-facts with a filter in ultrasound images according to some embodiments. Operations of the method are performed by processing logic that can comprise hardware (circuitry, dedicated logic, etc.), software (such as is run on a general-purpose computer system or a dedicated machine), firmware, or combinations thereof. The processing logic can be included in an ultrasound system. The ultrasound system can include an ultrasound scanner (e.g., transducer or probe), an ultrasound machine, a processor system, and a display device.

Ultrasound is transmitted at a patient anatomy and ultrasound data is generated based on reflections of the ultrasound from the patient anatomy (block 1402). An artifact signal is determined that is caused by an interferer and that corrupts the ultrasound data (block 1404). The processor system can determine the artifact signal based on the ultrasound data. Based on the artifact signal, artifact character-istics are determined, and the artifact characteristics can consist of, for example, an amplitude, a phase, a center frequency, and a bandwidth (block 1406). Based on the artifact characteristics, filter coefficients are generated (block 1408). Based on the filter coefficients, the ultrasound data is filtered to suppress the corruption caused by the artifact signal (block 1410). An ultrasound image is dis-played that is based on the ultrasound data after it has been filtered (block 1412).

In some embodiments, the display device displays an additional ultrasound image based on the ultrasound data before it has been filtered and receives a user selection to generate the filter coefficients and filter the ultrasound data. The processor system can generate, responsive to the user selection, the ultrasound image.

In some embodiments, the processor system implements a machine-learned model (e.g., a convolutional neural network) to generate, based on the ultrasound data before it has been filtered, an image quality score. The processor system can compare the image quality score to a threshold score. Filtering the ultrasound data can be responsive to the com-parison indicating the image quality score is below the threshold score.

FIG. 15 illustrates an example method 1500 that can be implemented by an ultrasound system for suppressing arti-facts with a filter in ultrasound images according to some embodiments. Operations of the method are performed by processing logic that can comprise hardware (circuitry, dedicated logic, etc.), software (such as is run on a general-purpose computer system or a dedicated machine), firmware, or combinations thereof. The processing logic can be included in an ultrasound system. The ultrasound system can include an ultrasound scanner (e.g., transducer or probe), an ultrasound machine, a processor system, and a display device.

Ultrasound is transmitted by an ultrasound scanner when the ultrasound scanner is detached from a patient and received data is generated, the received data including reflections of the ultrasound from a lens surface of the ultrasound scanner and artifacts caused by an interferer to the ultrasound system (block 1502). An artifact signal is determined by suppressing the reflections in the received data (block 1504). Based on the artifact signal, filter coef-ficients are generated (block 1506). Based on the filter coefficients, ultrasound data generated by the ultrasound system when the ultrasound scanner contacts the patient is filtered (block 1508). An ultrasound image is displayed, the ultrasound image based on the ultrasound data (block 1510).

5. Example Computing Device

FIG. 16 illustrates a block diagram of an example com-puting device 1600 that can perform one or more of the operations described herein, in accordance with some embodiments. Computing device 1600 can be connected to other computing devices in a LAN, an intranet, an extranet, and/or the Internet. The computing device can operate in the capacity of a server machine in client-server network environment or in the capacity of a client in a peer-to-peer network environment. The computing device can be implemented, at least in part, by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods and processes discussed herein. In some embodiments, the computing device 1600 may be one or more of an access point and a packet forwarding component.

The example computing device 1600 can include a processing device (e.g., a general-purpose processor, a PLD, etc.) 1602, a main memory 1604 (e.g., synchronous dynamic random-access memory (DRAM), read-only memory (ROM)), a static memory 1606 (e.g., flash memory and a data storage device 1618), which may communicate with each other via a bus 1630. Processing device 1602 can be implemented with one or more general-purpose processing devices such as a microprocessor, central processing unit, or the like. In an illustrative example, processing device 1602 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 1602 can also comprise one or more special-purpose processing devices such as an application specific integrated circuit (ASIC), a field programmable gate array (FPGA), a digital signal processor (DSP), network processor, or the like. The processing device 1602 may be configured to execute the operations described herein, in accordance with one or more aspects of the present disclosure, for performing the operations and steps discussed herein.

Computing device 1600 can further include a network interface device 1608 which may communicate with a network 1620. The computing device 1600 also can include a video display device 1610 (e.g., a liquid crystal display (LCD) or a cathode ray tube (CRT)), an alphanumeric input device 1612 (e.g., a keyboard), a cursor control device 1614 (e.g., a mouse) and/or an acoustic signal generation device 1616 (e.g., a speaker, and/or a microphone). In some embodiments, video display device 1610, alphanumeric input device 1612, and cursor control device 1614 are combined into a single component or device (e.g., an LCD touch screen).

Data storage device 1618 can include a computer-readable storage medium 1628 on which may be stored one or more sets of instructions 1626, e.g., instructions for carrying out the operations described herein, in accordance with one or more aspects of the present disclosure. For instance, the instructions 1626 can implement suppressing interference artifacts in ultrasound, as described herein. Instructions 1626 can also reside, completely or at least partially, within main memory 1604 and/or within processing device 1602 during execution thereof by computing device 1600, main memory 1604 and processing device 1602 also constituting computer-readable media. The instructions can further be transmitted or received over a network 1620 via network interface device 1608.

While computer-readable storage medium 1628 is shown in an illustrative example to be a single medium, the term "computer-readable storage medium" should be taken to include a single medium or multiple media (e.g., a centralized or distributed database and/or associated caches and servers) that store the one or more sets of instructions. In some embodiments, the computer-readable storage medium 1628 implements the suppressing interference artifacts in ultrasound, as described above. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

6. Example Machine-Learned Models

Many of the aspects described herein can be implemented using a machine-learned model. For the purposes of this disclosure, a machine-learned model is any model that accepts an input, analyzes and/or processes the input based on an algorithm derived via machine-learning training, and provides an output. A machine-learned model can be conceptualized as a mathematical function of the following form:

$$f(\hat{s}, \theta) = \hat{y} \qquad \text{Equation (1)}$$

In Equation (1), the operator f represents the processing of the machine-learned model based on an input and providing an output. The term $\hat{s}$ represents a model input, such as ultrasound data. The model analyzes/processes the input s using parameters $\theta$ to generate output $\hat{y}$ (e.g., object identification, object segmentation, object classification, etc.). Both $\hat{s}$ and $\hat{y}$ can be scalar values, matrices, vectors, or mathematical representations of phenomena such as categories, classifications, image characteristics, the images themselves, text, labels, or the like. The parameters $\theta$ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

FIG. 17 represents an example machine-learning architecture 1700 used to train a machine-learned model 1702 (e.g., a machine-learned model as previously described) in accordance with some embodiments. An input module 1704 accepts an input $\hat{s}$ 1706, which can be an array with members $\hat{s}1$ through $\hat{s}n$. The input $\hat{s}$ 1706 is fed into a training module 1708, which processes the input $\hat{s}$ 1706 based on the machine-learning architecture 1700. For example, if the machine-learning architecture 1700 uses a multilayer perceptron (MLP) model 1710, the training module 1708 applies weights and biases to the input $\hat{s}$ 1706 through one or more layers of perceptrons, each perceptron performing a fit using its own weights and biases according to its given functional form. MLP weights and biases can be adjusted so that they are optimized against a least mean square, log cosh, or other optimization function (e.g., loss function) known in the art. Although an MLP model 1710 is described here as an example, any suitable machine-learning technique can be employed, some examples of which include but are not limited to k-means clustering 1712, convolutional neural networks (CNN) 1714, a Boltzmann machine 1716, Gaussian mixture models (GMM), and long short-term memory (LSTM). The training module 1708 provides an input to an output module 1718. The output module 1718 analyzes the input from the training module 1708 and provides an output in the form of ŷ 1720, which can be an array with members ŷ1 through ŷm. The output ŷ 1720 can represent a known correlation with the input ŝ 1706, such as, for example, object identification, segmentation, and/or classification.

In some examples, the input ŝ 1706 can be a training input labeled with known output correlation values, and these known values can be used to optimize the output ŷ 1720 in training against the optimization/loss function. In other examples, the machine-learning architecture 1700 can categorize the output ŷ 1720 values without being given known correlation values to the inputs ŝ 1706. In some examples, the machine-learning architecture 1700 can be a combination of machine-learning architectures. By way of example, a first network can use the input ŝ 1706 and provide the output ŷ 1720 as an input ŝML to a second machine-learned architecture, with the second machine-learned architecture providing a final output ŷf. In another example, one or more machine-learning architectures can be implemented at various points throughout the training module 1708.

In some machine-learned models, all layers of the model are fully connected. For example, all perceptrons in an MLP model act on every member of ŝ. For an MLP model with a 100×100 pixel image as the input, each perceptron provides weights/biases for 10,000 inputs. With a large, densely layered model, this may result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

FIG. 18 represents an example model 1800 using a CNN to process an input image 1802, which includes representations of objects that can be identified via object recognition, such as people or cars (or an anatomy) in accordance with some embodiments. Convolution A 1804 can be performed to create a first set of feature maps (e.g., feature maps A 1806). A feature map can be a mapping of aspects of the input image 1802 given by a filter element of the CNN. This process can be repeated using feature maps A 1806 to generate further feature maps B 1808, feature maps C 1810, and feature maps D 1812 using convolution B 1814, convolution C 1816, and convolution D 1818, respectively. In this example, the feature maps D 1812 become an input for fully connected network layers 1820. In this way, the machine-learned model can be trained to recognize certain elements of the image, such as people, cars, or a particular patient anatomy, and provide an output 1822 that, for example, identifies the recognized elements. In some aspects, a secondary input can be appended to a feature map (e.g., feature map B 1808) generated by a neural network (e.g., CNN).

Although the example of FIG. 18 shows a CNN as a part of a fully connected network, other architectures are possible and this example should not be seen as limiting. There can be more or fewer layers in the CNN. A CNN component for a model can be placed in a different order, or the model can contain additional components or models. There may be no fully connected components, such as a fully convolutional network. Additional aspects of the CNN, such as pooling, downsampling, upsampling, or other aspects known to people skilled in the art can also be employed.

Unless specifically stated otherwise, terms such as "transmitting," "determining," "receiving," "generating," "or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general-purpose computing device selectively programmed by a computer program stored in the computing device. Such a computer program may be stored in a computer-readable non-transitory storage medium, such as a storage memory.

The methods and illustrative examples described herein are not inherently related to any particular computer or other apparatus. Various general-purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component.

Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

Reference in the specification to "one embodiment", "an embodiment", "one example", or "an example" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, or a combination of both. Although the processes are described below in terms of some sequential operations, it should be appreciated that some of the operations described may be performed in a different order. Moreover, some operations may be performed in parallel rather than sequentially.

In the specification, the term "and/or" describes three relationships between objects that may exist. For example, A and/or B may represent the following cases: only A exists, both A and B exist, and only B exist, where A and B may be singular or plural.

The foregoing description, for the purpose of explanation, has been described with reference to specific embodiments. However, the illustrative discussions above are not intended to be exhaustive or to limit embodiments of the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and embodiments of the invention are not to be limited to the details given herein, but may be modified within the scope and equivalents of the appended claims.

What is claimed is:

1. An ultrasound system comprising:
an ultrasound probe configured to transmit ultrasound at a patient anatomy and receive reflections of the ultrasound from the patient anatomy;
an ultrasound machine comprising a circuitry that is configured to generate received data including ultrasound data based on the reflections of the ultrasound and artifact data induced by an interferer that is external to the ultrasound system and the patient anatomy; and
a processor system comprising a processor implemented to:
separate the artifact data induced by the interferer from the ultrasound data including
instruct the ultrasound probe to cease the transmission of the ultrasound; and
reduce a system gain of the ultrasound machine while the transmission of the ultrasound is ceased to determine the artifact data;
determine, based on the artifact data, one or more artifact characteristics selected from the group consisting of an amplitude, a phase, a center frequency, and a bandwidth;
generate, based on the one or more artifact characteristics, filter coefficients; and
filter, based on the filter coefficients, the received data to suppress the artifact data and recover the ultrasound data.

2. The ultrasound system as described in claim 1, wherein the processor is further configured to enable at least one transducer element of the ultrasound probe for reception while the transmission is ceased to separate the artifact data from the ultrasound data.

3. The ultrasound system as described in claim 2, wherein the processor is further configured to:
receive a control signal; and
repeat the instruction to cease the transmission of the ultrasound and the enable the at least one transducer element for the reception in response to the control signal.

4. The ultrasound system as described in claim 1, wherein the processor is further configured to use a single transducer element of the ultrasound probe at a time to transmit and receive the ultrasound to determine the artifact data.

5. The ultrasound system as described in claim 1, wherein the processor is further configured to determine a summation of first data received from multiple transducer elements of the ultrasound probe to determine the artifact data.

6. The ultrasound system as described in claim 1, wherein the processor is further configured to:
beamform first data received from multiple transducer elements of the ultrasound probe to generate a beamformed signal; and
subtract the beamformed signal from second data received from a single transducer element of the ultrasound probe to determine the ultrasound data.

7. The ultrasound system as described in claim 1, wherein the processor is further configured to use a dedicated transducer element of the ultrasound probe to receive the artifact signal, wherein the dedicated transducer element is not configured to transmit the ultrasound to the patient anatomy.

8. The ultrasound system as described in claim 1, wherein the processor is further configured to:

instruct a user to detach the ultrasound probe from a patient having the patient anatomy;

cause the ultrasound probe to transmit additional ultrasound and receive additional reflections; and apply a time-gating function to the additional reflections to separate the artifact data from the ultrasound data.

9. The ultrasound system as described in claim 1, wherein the ultrasound probe is further configured to transmit the ultrasound at a first frequency, and the processor is further configured to filter the received signal with a notch filter having a notch based on the first frequency to separate the artifact data from the ultrasound data.

10. The ultrasound system as described in claim 9, wherein the ultrasound probe is further configured to transmit the ultrasound at a second frequency, and the processor system is further configured to:

filter the received signal with an additional notch filter having an additional notch based on the second frequency; and sum outputs of the notch filter and the additional notch filter to separate the artifact data from the ultrasound data.

11. The ultrasound system as described in claim 1, wherein the processor is further configured to repeat the separating the artifact data, the determining the one or more artifact characteristics, the generating the filter coefficients, and the filtering the received data for different lines of the ultrasound making up an ultrasound image frame.

12. The ultrasound system as described in claim 1, wherein the processor is further configured to repeat the separating the artifact data, the determining the one or more artifact characteristics, the generating the filter coefficients, and the filtering the received data for consecutive ultrasound image frames.

13. The ultrasound system as described in claim 1, wherein the processor is further configured to generate the filter coefficients based on at least one of a window function that determines a window length of the filter and a sparse coefficient function that determines the filter coefficients that are set to zero.

14. A machine-implemented method for an ultrasound system comprising an ultrasound probe, ultrasound machine, and a processor coupled to the ultrasound probe and the ultrasound machine, the method comprising:

transmitting, by the ultrasound probe, ultrasound at a patient anatomy;

receiving, by the ultrasound probe, reflections of the ultrasound from the patient anatomy;

generating, by a circuitry of the ultrasound machine, received data including ultrasound data based on the reflections of the ultrasound and artifact data induced by an interferer that is external to the ultrasound system and the patient anatomy;

separate, by the processor, the artifact data induced by the interferer from the ultrasound data including instructing, by the processor, the ultrasound probe to cease the transmission of the ultrasound; and reducing, by the processor, a system gain of the ultrasound machine while the transmission of the ultrasound is ceased;

determining, by the processor, one or more artifact characteristics selected from the group consisting of an amplitude, a phase, a center frequency, and a bandwidth based on the artifact data;

generating, by the processor, filter coefficients based on the one or more artifact characteristics; and filtering, by the processor, the received data to suppress the artifact data and recover the ultrasound data based on the filter coefficients.

15. The machine-implemented method as described in claim 14, further comprising: using a single transducer element of the ultrasound probe at a time to transmit and receive the ultrasound determine the artifact data.

16. The machine-implemented method as described in claim 14, further comprising:

determining, by the processor, a summation of first data received from multiple transducer elements of the ultrasound probe to determine the artifact data.

17. The machine-implemented method as described in claim 14, further comprising:

beamforming, by the processor, first data received from multiple transducer elements of the ultrasound probe to generate a beamformed signal; and subtracting, by the processor, the beamformed signal from second data received from a single transducer element of the ultrasound probe to determine the ultrasound data.

* * * * *